(12) United States Patent
Carneiro Gomes et al.

(10) Patent No.: US 11,887,704 B2
(45) Date of Patent: Jan. 30, 2024

(54) PROVIDING AND RECEIVING MEDICAL DATA RECORDS

(71) Applicant: Siemens Healthcare GmbH, Erlangen (DE)

(72) Inventors: Ricardo Daniel Carneiro Gomes, Mindelo (PT); Shiva Ashish Thumparthy, Karnataka (IN); Ilya Sher, Ramla (IL); Zeev Glozman, StGainesville, FL (US); Christoph Pedain, Munich (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 531 days.

(21) Appl. No.: 17/019,717

(22) Filed: Sep. 14, 2020

(65) Prior Publication Data
US 2021/0098091 A1    Apr. 1, 2021

(30) Foreign Application Priority Data
Sep. 30, 2019 (EP) ..................................... 19200368

(51) Int. Cl.
*G16H 10/60* (2018.01)
*G16H 40/20* (2018.01)
(Continued)

(52) U.S. Cl.
CPC ......... *G16H 10/60* (2018.01); *G06F 16/2255* (2019.01); *G16H 40/20* (2018.01); *H04L 9/3242* (2013.01); *G06Q 50/265* (2013.01)

(58) Field of Classification Search
None
See application file for complete search history.

(56) References Cited

U.S. PATENT DOCUMENTS 9,032,531 B1 * 5/2015 Scorvo ............... G06F 21/6254
                                                            726/25
9,866,393 B1 * 1/2018 Rush ..................... H04L 9/3236
(Continued)

FOREIGN PATENT DOCUMENTS

CN         109977261 A       7/2019

OTHER PUBLICATIONS

Almeida, Paulo Sergio et al. "Scalable Bloom Filters" Information Processing Letters, vol. 101, pp. 255-261, 2007.
(Continued)

*Primary Examiner* — Richard L Bowen
(74) *Attorney, Agent, or Firm* — Harness, Dickey & Pierce, P.L.C.

(57) ABSTRACT

A computer-implemented method provides a requested medical data record to a receiving entity. The method includes receiving a set of medical data records and receiving or initiating a joint data index and, for each medical data record of the set, applying a plurality of hash functions to a patient identifier corresponding to the medical data record to determine a hash vector, the patient identifier corresponding to the medical data record identifying the patient being subject of the medical data record, and updating the joint data index based on the hash vector. Furthermore, it includes providing the joint data index to the receiving entity and receiving a request for a record, corresponding to a request patient identifier and being based on the joint data index, from the receiving entity. The method includes providing the requested medical data record to the receiving entity via a secure communication channel.

18 Claims, 14 Drawing Sheets

(51) Int. Cl.
  *G06F 16/22*   (2019.01)
  *H04L 9/32*   (2006.01)
  *G06Q 50/26*   (2012.01)

(56) References Cited

U.S. PATENT DOCUMENTS

| | | | | |
|---|---|---|---|---|
| 10,102,233 | B1* | 10/2018 | Hurry | G16H 70/60 |
| 11,222,129 | B2* | 1/2022 | Linton | G06F 40/295 |
| 2010/0183018 | A1* | 7/2010 | Nikander | H04W 8/087 |
| | | | | 370/401 |
| 2013/0132408 | A1* | 5/2013 | Little | G06F 16/2255 |
| | | | | 707/754 |
| 2015/0149208 | A1* | 5/2015 | Lynch | G16H 10/60 |
| | | | | 705/3 |
| 2016/0342812 | A1* | 11/2016 | Lynch | H04W 12/02 |
| 2018/0210959 | A1* | 7/2018 | Khandelwal | G06F 16/2255 |
| 2020/0050595 | A1* | 2/2020 | Sun | G06F 16/2379 |
| 2020/0111578 | A1* | 4/2020 | Koblick | G16H 80/00 |
| 2020/0327250 | A1* | 10/2020 | Wang | G06N 20/00 |
| 2020/0342455 | A1* | 10/2020 | Poteet, III | G06Q 20/3829 |
| 2021/0098092 | A1* | 4/2021 | Katuwal | G06F 16/152 |

OTHER PUBLICATIONS

Extended European Search Report dated Feb. 17, 2020.
Vatsalan, Dinusha et al. "Privacy-preserving matching of similar patients" Journal of Biomedical Informatics, vol. 59, pp. 285-298, Feb. 2016. https://doi.org/10.1016/lbi.2015.12.004.

* cited by examiner

PROVIDING AND RECEIVING MEDICAL DATA RECORDS

PRIORITY STATEMENT

The present application hereby claims priority under 35 U.S.C. § 119 to European patent application number EP19200368.9 filed Sep. 30, 2019, the entire contents of which are hereby incorporated herein by reference.

FIELD

Embodiments of the invention generally relate to systems and/or methods for providing and receiving medical records.

BACKGROUND

For a single patient, it is common that the medical data records corresponding to the patient are not located in a single database or within a single entity, but distributed over different databases or entities. This is on the one hand due to the specialization into different medical practices (within a single entity like a hospital, but also with respect to different entities), but also due to a larger global mobility of the patients (due to long-term moves and delegations, or due to holidays and short time visits to other places, potentially distributed over several continents).

For diagnosis and treatment of patient, this poses a severe problem, because medical information must be first be located at a certain entity and transferred from this entity to the entity executing the current diagnosis or treatment, considering data privacy laws. If this is not possible (e.g., because the patient is unconscious), certain medical information must be recreated locally, or might even not be used for diagnosis and treatment, although it might be present in the database of another entity.

SUMMARY

One possible solution is to use a central database to store medical data records for all patients, at least of all patients in a certain geographical region or in a certain jurisdiction. However, the inventors have discovered that such a central data storage is a single point of failure, both with respect to availability, as well as with respect to security issues. Furthermore, the inventors have discovered that there might be data privacy regulations that might hinder the creation of such a central database, in particular a central database across different jurisdictions.

Another possible solution would be for a certain entity currently diagnosing or treating a certain patient to initiate requests to all other entities that potentially store medical information related to a patient. Equivalently, all entities could provide an information that they posses medical information with respect to a certain patient. However, the inventors have discovered that by using such a solution at least metadata related to patients is publicly available, and correlations may be used to draw certain conclusions with respect to a certain patient without his consent.

At least one embodiment of the present invention provides a solution for exchanging medical information between different entities, which at the same time minimizes the amount of metadata being publicly available.

Embodiments are directed to a method for providing a medical data record, a method for receiving a medical data record, a providing system, a receiving system, a computer-program product and a computer-readable medium. Further embodiments and advantageous embodiments are presented in the claims and in the specification.

The following the solutions according to embodiments of the invention is described with respect to the claimed systems (in particular, with respect to the providing system, the receiving system, the computer program and the computer-readable medium) as well as with respect to the claimed methods (in particular, with respect to the methods for providing and receiving a medical data record). Features, advantages or alternative embodiments herein can be assigned to the other corresponding claimed objects and vice versa. In other words, the systems can be improved with features described or claimed in the context of the corresponding method. In this case, the functional features of the methods are embodied by objective units of the systems.

Furthermore, the solutions according to embodiments of the invention is described with respect to methods and systems for providing a medical data record, with respect to methods and systems for receiving a medical data record, and with respect to methods and systems for transmitting a medical data record. Features, advantages or alternative embodiments herein can be assigned to the other corresponding claimed objects and vice versa. In other words, features of the methods and systems for providing a medical data record can be improved with features described or claimed in the context of methods and systems for receiving a medical data record or in the context of methods and systems for transmitting a medical data record. In particular, the medical data record provided by methods and systems for providing a medical data record can be received by methods and systems for receiving a medical data record. In particular, the methods and systems for transmitting a medical data record can be combinations of the methods and systems for providing a medical data record and of the methods and systems for receiving a medical data record.

A first embodiment of the invention relates to a computer-implemented method for providing a requested medical data record to a receiving entity. This method comprises receiving a set of medical data records stored in a database and receiving or initiating a joint data index. Furthermore, for each medical data record of the set of medical data records the method comprises applying a plurality of hash functions to a patient identifier corresponding to the medical data record to determine a hash vector, wherein the patient identifier corresponding to the medical data record identifies the patient being subject of the medical data record, and updating the joint data index based on the hash vector. Furthermore, the method comprises providing the joint data index to the receiving entity and receiving a request for the requested medical data record from the receiving entity, wherein the requested medical data record corresponds to a request patient identifier and wherein the request is based on the joint data index. Optionally, the method comprises verifying the request for the requested medical data record. Furthermore, the method comprises providing the requested medical data record to the receiving entity via a secure communication channel.

According to a second embodiment, the invention relates to a computer-implemented method for receiving a requested medical data record related to a patient from a selected providing entity. The method is based on receiving a request patient identifier corresponding to the patient and receiving a set of joint data indices, wherein each joint data index of the joint data indices corresponds to a providing entity from a group of providing entities, and wherein each joint data index of the joint data indices is based on a plurality of hash functions. The method furthermore comprises determining a hash vector by applying the plurality of hash functions to the request patient identifier; and determining a selected providing entity of the group of providing entities based on the hash vector and based on the joint data indices. Furthermore, the method comprises sending a request for the requested medical data record to the selected providing entity and, optionally, receiving the requested medical data record from the selected providing entity via a secure communication channel.

In particular, according to an embodiment, the invention can be considered to be a computer-implemented method for receiving a requested medical data record related to a patient from a selected providing entity, comprising:
  receiving a request patient identifier corresponding to the patient;
  receiving a set of Bloom filters, wherein each of the Bloom filters is a Bloom-filter of patient identifiers corresponding to the medical data records stored in the database of a providing entity from a group of providing entities;
  determining a hash vector by applying a group of hash functions to the request patient identifier;
  determining a selected providing entity of the group of providing entities based on the hash vector and based on the Bloom-filters;
  sending a request for the requested medical data record to the selected providing entity;
  receiving the requested medical data record from the selected providing entity via a secure communication channel.

According to a third embodiment, the invention relates to a computer-implemented method for transmitting a requested medical data record from a selected providing entity to a receiving entity. This method comprises receiving a set of medical data records stored in a database and receiving or initializing a joint data index by the selected providing entity. Furthermore, for each medical data record of the set of medical data records the method comprises applying a plurality of hash functions to a patient identifier corresponding to the medical data record to determine a hash vector, wherein the patient identifier corresponding to the medical data record identifies the patient being subject of the medical data record, and updating the joint data index based on the hash vector, both executed by the selected providing entity. Furthermore, the method comprises transmitting the joint data index from the selected providing entity to the receiving entity.

According to a fourth embodiment, the invention relates to a providing system for providing a requested medical data record to a receiving entity, comprising an interface and a computation unit,
  wherein the interface is configured for receiving a set of medical data records stored in a database;
  wherein the interface or the computation unit is furthermore configured for receiving or initializing a joint data index;
  wherein the computation unit is, for each medical data record of the set of medical data records,
    configured for applying a plurality of hash functions to a patient identifier corresponding to the medical data record to determine a hash vector, wherein the patient identifier corresponding to the medical data record identifies the patient being subject of the medical data record;
    and configured for updating the joint data index based on the hash vector;
  wherein the interface is furthermore configured for providing the joint data index to the receiving entity,
  wherein the interface is furthermore configured for receiving a request for the requested medical data record from the receiving entity, wherein the requested medical data record corresponds to a request patient identifier,
  wherein the computation unit is optionally configured for verifying the request for the requested medical data record,
  wherein the interface is furthermore configured for providing the requested medical data record to the receiving entity via a secure communication channel.

According to a fifth embodiment, the invention relates to a receiving system for receiving a requested medical data record related to a patient from a selected providing entity, comprising an interface and a computation unit,
  wherein the interface is configured for receiving a request patient identifier corresponding to the patient;
  wherein the interface is furthermore configured for receiving a set of joint data indices, wherein each joint data index of the joint data indices corresponds to a providing entity from a group of providing entities;
  wherein the computation unit is configured for determining a hash vector by applying a group of hash functions to the request patient identifier;
  wherein the computation unit is furthermore configured for determining a selected providing entity of the group of providing entities based on the hash vector and based on the joint data indices;
  wherein the interface is furthermore configured for sending a request for the requested medical data record to the selected providing entity;
  wherein the interface is furthermore configured for receiving the requested medical data record from the selected providing entity via a secure communication channel.

According to a sixth possible embodiment, the invention relates to a transmission system, wherein the transmission system comprises a providing system according to the fourth embodiment of the invention, and wherein the transmission system comprises a receiving system according to the fifth embodiment of the invention. In particular, the transmission system is configured for executing the method for transmitting a requested medical data record. The transmission system is configured for executing the method for transmitting a requested medical data record by the providing system (in particular, by the interface and the computation unit of the providing system) and the receiving system (in particular, by the interface and the computation unit of the receiving system) being configured to executed the respective method steps.

According to a seventh embodiment, the invention relates to a computer program comprising instructions which, when the program is executed by a providing system, cause the providing system to carry out the method for providing a requested medical data record according to the invention and its embodiments; and/or which, when the program is executed by a receiving system, cause the receiving system to carry out the method for receiving a requested medical data record according to the invention and its embodiments.

According to a possible eighth embodiment, the invention relates to a computer program comprising instructions which, when the program is executed by a providing system, cause the providing system to carry out the method for providing a requested medical data record according to the invention and its embodiments.

According to a possible ninth embodiment, the invention relates to a computer program comprising instructions which, when the program is executed by a receiving system, cause the receiving system to carry out the method for receiving a requested medical data record according to the invention and its embodiments.

According to a possible tenth embodiment, the invention relates to a computer program comprising instructions which, when the program is executed by a transmission system, cause the transmission system to carry out the method for transmitting a requested medical data record according to the invention and its embodiments.

According to a eleventh embodiment, the invention relates to a computer-readable medium comprising instructions which, when executed by a providing system, cause the providing system to carry out the method for providing a requested medical data record according to the invention and its embodiments; and/or which, when executed by a receiving system, cause the receiving system to carry out the method for receiving a requested medical data record according to the invention and its embodiments.

According to a possible twelfth embodiment, the invention relates to a computer-readable medium comprising instructions which, when executed by a providing system, cause the providing system to carry out the method for providing a requested medical data record according to the invention and its embodiments.

According to a possible thirteenth embodiment, the invention relates to a computer-readable medium comprising instructions which, when executed by a receiving system, cause the receiving system to carry out the method for receiving a requested medical data record according to the invention and its embodiments.

According to a possible fourteenth embodiment, the invention relates to a computer-readable medium comprising instructions which, when executed by a transmission system, cause the transmission system to carry out the method for transmitting a requested medical data record according to the invention and its embodiments.

According to another embodiment, the invention relates to a computer-implemented method for providing a requested medical data record to a receiving entity, comprising:

receiving a set of medical data records stored in a database;

receiving or initializing a joint data index;

for each respective medical data record of the set of medical data records applying a plurality of hash functions to a patient identifier corresponding to the respective medical data record to determine a respective hash vector, the patient identifier corresponding to the respective medical data record identifying the patient being subject of the respective medical data record, and updating the joint data index based on the respective hash vector;

providing the joint data index to the receiving entity;

receiving a request for the requested medical data record from the receiving entity, the request being based on the joint data index and the requested medical data record corresponding to a request patient identifier; and providing the requested medical data record to the receiving entity via a secure communication channel.

According to another embodiment, the invention relates to a computer-implemented method for sending a request for a requested medical data record of a patient, comprising:

receiving a request patient identifier corresponding to the patient;

receiving a set of joint data indices, each respective joint data index of the set of joint data indices respectively corresponding to a respective providing entity from a group of providing entities, wherein each respective joint data index of the set of joint data indices is based on a plurality of hash functions;

determining a hash vector by applying the plurality of hash functions to the request patient identifier;

determining a selected providing entity of the group of providing entities based on the hash vector and based on the joint data indices; and sending a request for the requested medical data record to the selected providing entity.

According to another embodiment, the invention relates to a providing system for providing a requested medical data record to a receiving entity, comprising:

an interface, configured to receive a set of medical data records stored in a database; and a computation unit, wherein the interface or the computation unit is configured to receive or initialize a joint data index and wherein the computation unit is, for each respective medical data record of the set of medical data records, configured to apply a plurality of hash functions to a patient identifier corresponding to the respective medical data record to determine a respective hash vector, the patient identifier corresponding to the respective medical data record identifying the patient being subject of the respective medical data record, and configured to update the joint data index based on the respective hash vector;

wherein the interface is furthermore configured to provide the joint data index to the receiving entity, wherein the interface is furthermore configured to receive a request for the requested medical data record from the receiving entity, wherein the requested medical data record corresponds to a request patient identifier, and wherein the interface is furthermore configured to provide the requested medical data record to the receiving entity via a secure communication channel.

According to another embodiment, the invention relates to a receiving system for receiving a requested medical data record related to a patient from a selected providing entity, comprising:

an interface configured to receive a request patient identifier corresponding to the patient and configured to receive a set of joint data indices, each respective joint data index of the set of joint data indices corresponding to a providing entity from a group of providing entities; and a computation unit configured to determine a hash vector by applying a group of hash functions to the request patient identifier, determine a selected providing entity of the group of providing entities based on the hash vector and based on the joint data indices, wherein the interface is further configured to send a request for the requested medical data record to the selected providing entity and is further configured to receive the requested medical data record from the selected providing entity via a secure communication channel.

According to another embodiment, the invention relates to a non-transitory computer program product storing instructions of a program which, when the program is executed by a providing system, cause the providing system to carry out the method of an embodiment; and/or which, when the program is executed by a receiving system, cause the receiving system to carry out the method of an embodiment.

According to another embodiment, the invention relates to a non-transitory computer-readable medium storing instructions of a program which, when executed by a providing system, cause the providing system to carry out the method of an embodiment; and/or which, when executed by a receiving system, cause the receiving system to carry out the method of one an embodiment.

BRIEF DESCRIPTION OF THE DRAWINGS

The properties, features and advantages of this invention described above, as well as the manner they are achieved, become clearer and more understandable in the light of the following description and embodiments, which will be described in detail in the context of the drawings. This following description does not limit the invention on the contained embodiments. Same components or parts can be labeled with the same reference signs in different figures. In general, the figures are not for scale. In the following.

DETAILED DESCRIPTION OF THE EXAMPLE EMBODIMENTS

Figure 1:
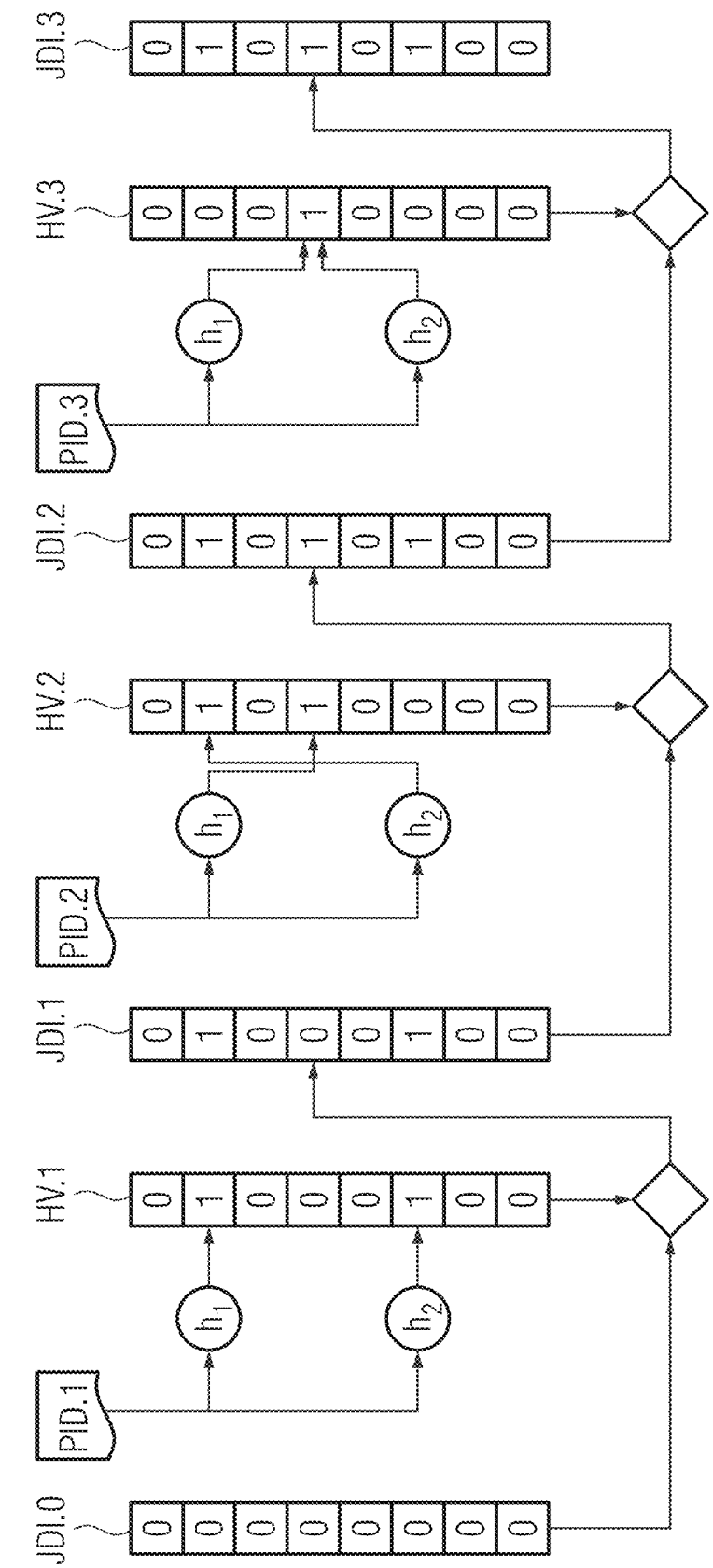
FIG. 1 displays a first embodiment for updating a joint data index.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Bluray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A first embodiment of the invention relates to a computer-implemented method for providing a requested medical data record to a receiving entity. This method comprises receiving a set of medical data records stored in a database and receiving or initiating a joint data index. Furthermore, for each medical data record of the set of medical data records the method comprises applying a plurality of hash functions to a patient identifier corresponding to the medical data record to determine a hash vector, wherein the patient identifier corresponding to the medical data record identifies the patient being subject of the medical data record, and updating the joint data index based on the hash vector. Furthermore, the method comprises providing the joint data index to the receiving entity and receiving a request for the requested medical data record from the receiving entity, wherein the requested medical data record corresponds to a request patient identifier and wherein the request is based on the joint data index. Optionally, the method comprises verifying the request for the requested medical data record. Furthermore, the method comprises providing the requested medical data record to the receiving entity via a secure communication channel.

In particular, in an embodiment the step of receiving the set of medical data records is executed by an interface. In particular, the step of receiving or initializing the joint data index is executed by the interface or by a computation unit. In particular, the steps of applying the plurality of hash functions and of updating the joint data index are executed by the computation unit. In particular, the steps of providing the joint data index of receiving a request for the requested medical data record are executed by the interface. In particular, the optional step of verifying the request is executed by the calculation unit. In particular, the step of providing the requested medical data record is executed by the interface. In particular, the interface is an interface of a providing entity and/or a providing system, and the calculation unit is a calculation unit of the providing entity and/or the providing system.

In this description, the term "providing entity" is used for describing an entity (e.g., a physician, a hospital or a group of hospitals) that stores and eventually shares medical data records corresponding to patients. Furthermore, the term "receiving entity" is used for describing an entity (e.g., a physician, a hospital, a group of hospitals or a patient) that requests and eventually receives medical data records from a providing entity. The term "providing system" is used for describing a technical system (in particular IT equipment) of the providing entity for executing methods according to the invention (in particular for storing and/or sharing medical data records), and the term "receiving system" is used for describing a technical system (in particular IT equipment) of the receiving entity for executing methods according to the invention (in particular for requesting and/or receiving medical data records). The term "transmission system" is used for describing a technical system comprising at least one providing system and at least one receiving system.

The terms "providing entity" and "providing system" can be used as synonyms in situations clear for a person skilled in the art. The terms "receiving entity" and "receiving system" can be used as synonyms in situations clear for a person skilled in the art.

In an embodiment, the step of receiving the set of medical data records can be executed before, after or in parallel to the step of receiving or initializing the joint data index. In particular, the steps of applying the plurality of hash functions and the updating the joint data index are executed after the steps of receiving the set of medical data records and the step of receiving or initializing the joint data index.

For each medical data record of the set of medical data records, the step of updating the joint data index is executed after the step of applying the plurality of hash functions. It is possible that both steps are executed for one of the medical data records, before the steps are executed for another medical data record. Alternatively, the step of applying the plurality of hash functions can be executed for all medical data records of the set of medical data records, and only afterwards the step of updating the joint data index is executed for all medical data records of the set of medical data records.

In particular, the step of providing the joint data index is executed after all steps of updating the joint data index. In particular, the remaining steps of receiving the request for the requested medical data record, the optional step of verifying the request, and the step of providing the requested medical data record are executed after the step of providing the joint data index and in the order used in the claims or in the description.

In particular, a joint data index is a dataset based on a set of patient identifiers which allows to exclude that a certain patient identifier is part of the set of patient identifiers. In particular, based on the joint data index it cannot be determined that the certain patient identifier is a part of the set of patient identifiers. In other words, a joint data index allows for false positives, but not for false negatives.

In particular, the joint data index can be a combinable joint data index. For a combinable joint data index, the joint data index $I(S_1+S_2)$ of a set union of a first set $S_1$ of patient identifiers and a second set $S_2$ of patient identifiers can be calculated based on the joint data index $I(S_1)$ of the first set of patient identifiers and the joint data index $I(S_2)$ of the second set of patient identifiers, $I(S_1+S_2)=f(I(S_1), I(S_2))$. In particular, the joint data index $I(S_1+S_2)$ of a set union of a first set $S_1$ of patient identifiers and a second set $S_2$ of patient identifiers can be calculated as an OR-Operation or as a sum of the joint data index $I(S_1)$ of the first set of patient identifiers and the joint data index $I(S_2)$ of the second set of patient identifiers, so $I(S_1+S_2)=I(S_1)$ OR $I(S_2)$ or $I(S_1+S_2)=I(S_1)+I(S_2)$.

In particular, the joint data index can be an n-dimensional vector. In particular, the above-mentioned operations of joint data indices can be understood as element-wise operations, e.g., $I_j(S_1+S_2)=f(I_j(S), I_j(S_2))$, $I_j(S_1+S_2)=I_j(S_1)$ OR $I_j(S_2)$ or $I_j(S_1+S_2)=I_j(S)+I_j(S_2)$ for integer j between 1 and n.

In particular, receiving the joint data identifier can be equivalent with accessing a joint data identifier stored on a memory unit of the providing system. In particular, receiving the joint data identifier can be equivalent with initializing the joint data identifier, so that the initialized joint data identifier corresponds to an empty database of medical data records. In particular, initializing the joint data index can comprise assigning the value "0" or "false" to all elements of the joint data index.

In particular, a request based on the joint data index does not necessarily comprise the joint data index, and the content of the request does not necessarily depend on the joint data index. In particular, a request can be based on the joint data index, if the existence and/or the creation of the request is based on the joint data index.

A patient identifier can generally be used to unambiguously identify the patient. In particular, the patient identifier can comprise the name of the patient, the data of birth of the patient and/or an ID of the patient (e.g. the social insurance number, the ID number, a driving license number, or a passport number). In particular, the patient identifier can comprise an identifier of a device used by the patient, e.g. the IP (acronym for "Internet Protocol") address, the IMEI (acronym for "International Mobile Equipment Identity"), the MAC (acronym for "Media Access Control") address of the device (e.g. a computer or a mobile device) used by the patient. In particular, the patient identifier can be based on a public key or on a private key related with the patient. In particular, the patient identifier can also be a shared secret or token. The term "patient identifier" is equivalent to the term "identifier of the patient". Furthermore, instead of the term "patient identifier" the short term "identifier" can be used.

In particular, the patient identifier corresponding to a medical data record is the patient identifier of a patient being subject of the medical data record. In particular, the patient identifier corresponding to a medical data record can be contained in the medical data record.

The request patient identifier may be identical to one of the patient identifiers corresponding to the medical data records stored in the database, but the request patient identifier may also be different from all of the patient identifiers corresponding to the medical data records stored in the database.

A medical data record in general comprises medical data of at least one patient. The terms "medical data record", "medical record", "medical dataset", "medical data", "clinical data record", "clinical record", "clinical dataset", "clinical data" can be used as synonyms throughout this document.

The medical data record can comprise a medical image dataset. Such medical image dataset is acquired from the patient using a medical imaging apparatus, e.g. a magnetic resonance apparatus, a single-photon emission tomography (SPECT) apparatus, a positron emission tomography (PET) apparatus, a computed tomography apparatus, an ultrasound apparatus, an X-ray apparatus, a C-arm apparatus or a combined medical imaging apparatuses formed by any combination composed of the aforementioned imaging modalities. The medical image dataset can also comprise automatically, semi-automatically or manually generated processing information, such as segmented organs, contour information, registration information, etc.

The medical data record can also comprise medical data acquired or derived from other medical apparatuses which are not medical imaging apparatuses. Such other medical apparatuses can e.g. be a treatment apparatus, e.g. a radiotherapy device, a lithotripsy device, a laser treatment device, an infusion pump or an interventional treatment device. The medical data record can also stem from an apparatus for intensive medicine, a mobile monitoring device, a respiratory device, an anesthetic machine, an ECG device, an EEG device, a blood pressure measurement device, an infusion device or a dialysis device. The medical data record can also comprise laboratory diagnostics or genetic information.

The medical data record can also comprise a complete or part of an electronic health record of a patient. Therefore, the medical data record can comprise information about a disease history of the patient. The medical data record can also contain annotation information, which describes automatically, semi-automatically or manually generated diagnostic findings in the medical data record. The medical data record can also comprise demographic metadata related to the patient, such as gender, age, weight, size, etc.

Other medical data which can be considered by those skilled in the art can also be part of the medical data record.

The medical data record may only be a pointer to a specific location in a storage database in which medical data are stored. This storage database can be a central database, cloud storage, or a distributed database. In this case, access to the medical data record means access to the pointer so that using the pointer the medical data which are stored in the storage database can be accessed.

A set of medical data records can comprise one medical data record and/or a plurality of medical data records. A set of medical data records can also be an empty set.

In particular, a hash of a dataset is the result of the application of a hash function on the dataset or a combination of the dataset and other data. In particular, the hash function can take other arguments, for example a seed.

In general, a hash function is a function that maps data of arbitrary size to data of a fixed size. In particular, the hash function is a cryptographic hash function. In particular, a cryptographic hash function is a deterministic function; in particular the output of the hash function does only depend on the input of the hash function. In particular, a cryptographic hash function can be calculated in a fast manner for all input values. In particular, a cryptographic hash function is only brute-force invertible, i.e. given the output of a cryptographic hash function it is only possible to calculate the corresponding input of the cryptographic hash function by calculating the cryptographic hash function for an large amount of input values (i.e. a brute-force attack). In other words, finding the input value corresponding to the output value of a cryptographic hash function is an intractable problem. In particular, finding a first input value and a second input value of a cryptographic hash function that lead to an identical output value is an intractable problem. In particular, a cryptographic hash function is scattering; i.e. even correlated inputs of the cryptographic hash function lead to uncorrelated outputs of the cryptographic hash function.

In particular, a hash function can calculate a Merkle root of the input data, in particular by computing hashes within a Merkle tree.

In particular, a hash function can also be a subset of another hash function, meaning that the result of the hash function applied to a dataset is a subset of the result of the another hash function applied to that dataset. In particular, the subset of the result of the another hash function can be a certain bit or a certain byte of the result of the another hash function.

In particular, one or more of the following hash functions can be used: "Snefru", "N-Hash", "FFT-Hash", "MD4", "MD5", "SHA" (in particular "SHA-0", "SHA-1", "SHA-256", "SHA-384" and "SHA-512"), "RIPEMD", "HAVAL", "TIGER", "PANAMA", "WHIRLPOOL", "SMA SH", "FORK-256", "SHA-3", "BLAKE", or other hash functions based on the Merkle-Damgerd construction or on the Sponge construction.

The plurality of hash functions can also be based on a smaller number of hash functions, by subdividing the results of the smaller number of hash functions. For example, if a hash function results in a result with N bits, two other hash functions can be defined, wherein the first other hash functions maps the input to the first N/2 bits of the original hash function, and wherein the second other hash function maps the input to the second N/2 bits of the original hash function. An arbitrary number of hash functions can be generated in a similar manner.

In particular, a hash vector is a vector comprising different hashes of the same dataset. In particular, each entry of the hash vector is the result of applying one of a plurality of hash functions to the dataset. If the hash vector is an n-dimensional vector, each entry of the hash vector is the result of applying one of n hash functions to the data set, without using the same hash function twice. In particular, the dimensionality of the hash vector is equal to the dimensionality of the joint data index. In particular, a hash vector of a dataset is the joint data index of only this data set.

It is not necessary that the hash vector is stored in the memory as consecutive vector, the hash vector can also be stored distributed amongst the file system. In particular, the term "hash vector" and the term "hash set" or "set of hashes" can be used as synonyms throughout this document.

In particular, a secure communication channel is a way of transferring data that is resistant to overhearing and/or tampering. Examples for a secure communication channel are the use of an Intranet, the use of a VPN (acronym for "Virtual Private Network") the use of an encrypted communication (for example based on an asymmetric encryption) in particular via the internet, the use of HTTPS (acronym for "Hypertext Transfer Protocol Secure") or FTPS (acronym for "File Transfer Protocol Secure").

The optional step of verifying the request for the requested medical data record can comprise verifying that the database contains at least one medical data record related to the request patient identifier. In particular, the requested medical data record can be identical with the at least one medical data record. Furthermore, the optional step of verifying the request for the requested medical data record can comprise checking whether the requesting entity is entitled to access the requested medical data record. For example, the requesting entity may only be allowed to access the requested medical data record if the requesting entity is located in a certain jurisdiction, or if the patient corresponding to the request patient identifier gave its consent that the requesting entity is allowed to access the requested medical data record. In particular, if the step of verifying results in a positive outcome, the step of providing the requested medical data record to the receiving entity will be executed, and if the step of verifying results in a negative outcome, the step of providing the requested medical data record to the receiving entity will not be executed.

The inventors recognized that by providing only a joint data index it is not possible for any other entity to determine whether data related to a certain patient is stored in the database. This increases the data security and the data privacy for the patient data, because less metadata of patients is publicly available. This is due to publicly available metadata of patients can give various hints about their actual data (e.g. knowing that a certain patient has a data record at an oncologist or a psychologist might indicate that this patient has oncological or psychological problems; furthermore, correlations in metadata can be used to identify patients although only anonymized identifiers are used).

At the same time, by providing the joint data index to a receiving entity, the receiving entity may check before sending a request for a certain data record whether the providing entity stores a medical data record related to a certain patient, at least with a certain probability. In particular, using the joint data index the receiving entity may restrict the set of providing entities which possibly store data related to a certain patient, so that the receiving entity can reduce the number of requests to providing entities. By reducing the number of requests also the metadata publicly communicated may be reduced.

According to a further embodiment of the invention each of the hash functions maps the patient identifier to one element of the hash vector. In particular, the elements of the hash vector the patient identifier is mapped to by one of the hash functions are assigned with a first value (in particular the value "1" or "true"), and the elements of the hash vector the patient identifier is not mapped to by one of the hash functions are assigned with a second value (in particular the value "0" or "false").

The inventors recognized that by using hash functions that map patient identifiers to elements of the hash vector the patient identifier can be encoded in a memory-efficient way.

According to a further possible embodiment of the invention, the joint data index and the hash vector comprise the same number of Boolean or integer elements, and updating the joint data index based on the hash vector is based on an element—wise logic or—combination of the joint data index to be updated and the hash vector or on an element-wise sum of the joint data index to be updated and the hash vector.

The inventors have recognized that by using an element—wise logic or—combination several patient identifiers can be encoded in a joint data index in a memory-efficient way.

According to a further embodiment of the invention the joint data index provided to the receiving entity is a Bloom filter of the patient identifiers corresponding to the medical data records stored in the database. In particular, a Bloom filter is a space-efficient probabilistic data structure that can be used for testing whether an element is a member of a set.

In particular, according to this embodiment, the invention can be considered to be a computer-implemented method for providing a requested medical data record to a receiving entity, comprising receiving a set of medical data records stored in a database, providing a joint data index to the receiving entity, wherein the joint data index is a Bloom-filter of patient identifiers corresponding to the medical data records stored in the database, receiving a request for the requested medical data record from the receiving entity, optionally, verifying the request for the requested medical data record, and providing the requested medical data record to the receiving entity via a secure communication channel.

The inventors recognized that a Bloom filter has a strong memory space advantage over other data structures for representing sets, in particular for sets with memory-large elements like patient identifiers. In particular, a Bloom filters does not comprise a single element of the underlying set at all. Furthermore, for a Bloom filter the time needed either to add items or to check whether an item is in the set is a fixed constant, and not dependent on the size of the underlying set.

According to a further embodiment of the invention, the Bloom filter is a counting Bloom filter, a scalable Bloom filter, a layered Bloom filter and/or an attenuated Bloom filter.

A counting Bloom filter is a Bloom filter with integer elements (in contrast to binary/Boolean elements in a standard Bloom filter). For updating a Bloom filter with an additional patient identifier, the elements of the Bloom filter the additional elements are mapped to are incremented by 1. Using a counting Bloom filter has the advantageous that patient identifiers corresponding to medical data records removed from the database can also be removed from the Bloom filter, my decrementing the respective elements of the Bloom filter by 1. Using a counting Bloom filter has the disadvantageous that the memory consumption of a counting Bloom filter is higher than the memory consumption of a standard Bloom filter (due to using integer variables instead of Boolean variables).

A scalable Bloom filter can adapt dynamically to the number of patient identifiers corresponding to the medical data records stored in the database. In particular, a scalable Bloom filter is based on sequences of standard Bloom filters with increasing capacity and tighter false positive probabilities, so as to ensure that a maximum false positive probability can be set beforehand, regardless of the number of elements to be inserted. Details about scalable Bloom filters can be found in P. Almeida et al., "Scalable Bloom Filters" (2007), Information Processing Letters (2007), 101(6):255-261, the entire contents of which are hereby incorporated herein by reference.

In particular, a layered Bloom filter consists of multiple Bloom filter layers. Layered Bloom filters allow keeping track of how many times an item was added to the Bloom filter by checking how many layers contain the item.

In particular, an attenuated Bloom filter of depth D can be interpreted as an array of D normal Bloom filters. In the context of service discovery in a network, each node stores regular and attenuated Bloom filters locally. The regular or local Bloom filter indicates which services are offered by the node itself. The attenuated filter of level i indicates which services can be found on nodes that are i-hops away from the current node. The i-th value is constructed by taking a union of local Bloom filters for nodes i-hops away from the node.

According to a further embodiment of the invention providing the joint data identifier to the receiving entity comprises storing the joint data identifier in a distributed ledger. In particular, the actions of "providing the joint data identifier to the receiving entity" is equivalent with "storing the joint data identifier in a distributed ledger".

In general, a distributed ledger is a decentralized database. In particular, the distributed ledger is distributed in the sense that there are several copies of (at least parts of) the distributed ledger in different memory units, wherein the memory units are spatially or geographically distributed. The distributed ledger comprises multiple records, wherein the multiple records can be identified with database entries. In particular, the multiple records are organized as data blocks. In particular, the records are created by different entities, in particular different nodes of a network, and stored with the different entities, in particular within the different nodes of the records. In other words, the construction and maintenance of the records is typically not performed by a central authority, but independently by nodes of the network. In typical cases, each node of the network maintains a local copy of the distributed ledger.

In general, updating the distributed ledger is typically based on a consensus mechanism, wherein a consensus mechanism ensures that the different copies of the distributed ledger match, also in the cases of a delayed communication between the entities storing the copies of the distributed ledger.

In particular, storing data in a distributed ledger can comprise appending a further data block to the distributed ledger, wherein the further data block comprises the data to be stored. Appending a further data block to the distributed ledger can comprise executing the consensus mechanism, wherein executing the consensus mechanism can comprise a proof of work, a proof of storage, a proof of stake, and/or a proof of elapsed time. A proof of work can be a compute-bound proof of work, a network-bound proof of work and/or a memory-bound proof of work.

In particular, a distributed ledger can be a blockchain, a blocktree and/or a tangle.

The inventors recognized that by providing the joint data index in a distributed ledger the access times (e.g. due to network latency) for accessing the joint data index by an external entity decreases due to the distributed way of storing, and there is redundancy in the system, so that the joint data index can be accessed by an external entity even if one or a subset of nodes storing the distributed ledger are offline (e.g. to maintenance). At the same time, by using a distributed ledger, it can be ensured that the joint data indices are consistent, so that there is no fork between different nodes storing the distributed ledger. In particular, using a distributed ledger one has a single point of truth, but not a single point of failure.

According to a further embodiment of the invention, the request comprises a salted hash of the request patient identifier and/or a signature signed with a private key related to the request patient identifier.

In particular, a salted hash of the request patient identifier is a hash of the request patient identifier combined with a random dataset. The random dataset may be shared between the receiving entity and a providing entity. By using a salted hash the actual hash can be disguised from third entities, so that it becomes harder to utilize metadata for de-anonymizing or correlating data.

In particular, the signature is a digital signature. In general a digital signature relies on an asymmetric key pair comprising a private key and a public key, originating from an asymmetrical cryptography system. A public key is corresponding with a private key or vice versa, if the private key and the public key form an asymmetric key pair.

In particular, a digital signature is the output of a signing algorithm, wherein the signing algorithm takes as first input the data to be signed (also denoted as "message") and as second input a signing information. In particular, the signing information is a private key. In particular, a signature is signed with a private key, if the private key was used as second input for the signing algorithm when creating the signature. In particular, a signature is based on certain data, if the certain data was used as first input for the signing algorithm when creating the signature.

In particular, for a signing algorithm there exists a signature verifying algorithm, wherein the signature verifying algorithm takes as input a dataset, a signature and a public key, and wherein the output of the signature verifying algorithm determines whether the given signature is the output of the signing algorithm applied to the dataset with a private key corresponding to the given public key.

In particular, the signature verifying algorithm can verify the validity of a signature without the knowledge of the private key corresponding to the public key. In particular, a private key used to sign a signature cannot be deduced from the signature.

In particular, the patient identifier can be identical to the public key or stored related to the public key.

The inventors recognized that by using a digital signature an authorization for accessing a medical data record can be proven, in particular if only the patient has access to the private key corresponding to the patient identifier identifying him or her.

According to a second embodiment, the invention relates to a computer-implemented method for receiving a requested medical data record related to a patient from a selected providing entity. The method is based on receiving a request patient identifier corresponding to the patient and receiving a set of joint data indices, wherein each joint data index of the joint data indices corresponds to a providing entity from a group of providing entities, and wherein each joint data index of the joint data indices is based on a plurality of hash functions. The method furthermore comprises determining a hash vector by applying the plurality of hash functions to the request patient identifier; and determining a selected providing entity of the group of providing entities based on the hash vector and based on the joint data indices. Furthermore, the method comprises sending a request for the requested medical data record to the selected providing entity and, optionally, receiving the requested medical data record from the selected providing entity via a secure communication channel.

In particular, in an embodiment the step of receiving the request patient identifier is executed by an interface. In particular, the step of determining the hash vector and the step of determining a selected providing entity is executed by a calculation unit. In particular, the steps of sending the request for the requested medical data record and of receiving the requested medical data record are executed by the interface. In particular, the interface is an interface of a receiving system, and the calculation unit is a calculation unit of the receiving system.

The inventors recognized that by using the hash vector to determine the selected providing entity, it is not necessary to send a request to a providing entity that for sure does not contain a medical data record corresponding to the patient identifier. This reduces the number of necessary data transmissions and increases the efficiency of the transfers of medical data records. Furthermore, the available metadata and therefore the possibility to de-anonymize patients or determine correlations is reduced.

According to a further embodiment of the invention, the step of determining the selected providing entity comprises an elementwise comparison between the hash vector and each of the joint data indices. In particular, each element of the hash vector can take a first value or a second value (for example the first value can be "0"/"false", and the second value can be "1"/"true"), and in the element-wise comparison it is determined that for every element of the hash vector comprising taking a second value, the corresponding element of the joint data index takes a predefined value. In particular, the predefined value can be the second value or an integer fulfilling a certain condition (in particular, the condition can be that the integer is larger than 1).

The inventors recognized that by using an elementwise comparison between the hash vector and the joint data index the comparison can be executed very efficient. Furthermore, using the element-wise comparison joint data indices representing data bases not containing medical data records corresponding to the request patient identifier can be excluded in an efficient manner.

According to a further embodiment of the invention each joint data index of the joint data indices is a Bloom filter of patient identifiers corresponding to medical data records stored by the providing entity corresponding to the joint data index. In particular, the medical data records are stored in a database of the providing entity.

In particular, according to an embodiment, the invention can be considered to be a computer-implemented method for receiving a requested medical data record related to a patient from a selected providing entity, comprising:
  receiving a request patient identifier corresponding to the patient;
  receiving a set of Bloom filters, wherein each of the Bloom filters is a Bloom-filter of patient identifiers corresponding to the medical data records stored in the database of a providing entity from a group of providing entities;
  determining a hash vector by applying a group of hash functions to the request patient identifier;
  determining a selected providing entity of the group of providing entities based on the hash vector and based on the Bloom-filters;
  sending a request for the requested medical data record to the selected providing entity;
  receiving the requested medical data record from the selected providing entity via a secure communication channel.

The inventors recognized that a Bloom filter has a strong memory space advantage over other data structures for representing sets, in particular for sets with memory-large elements like patient identifiers. In particular, a Bloom filters does not comprise a single element of the underlying set at all. Furthermore, for a Bloom filter the time needed either to add items or to check whether an item is in the set is a fixed constant, and not dependent on the size of the underlying set.

According to a further embodiment of the invention receiving the set of joint data indices comprises querying a distributed ledger storing the set of joint data indices.

The inventors recognized that by receiving the joint data index from a distributed ledger the access times (e.g. due to network latency) for accessing the joint data index decreases due to the distributed way of storing, and there is redundancy in the system, so that the joint data index can be accessed even if one or a subset of nodes storing the distributed ledger are offline (e.g. to maintenance), or if a subset of the providing entities is offline. At the same time, by using a distributed ledger, it can be ensured that the joint data indices are consistent, so that there is no fork between different nodes storing the distributed ledger. In particular, using a distributed ledger one has a single point of truth, but not a single point of failure.

According to a further embodiment of the invention within the method for receiving a requested medical data record the requested medical data record is provided by the selected providing entity according to a method for providing a requested medical data record according to the invention and its embodiments and/or embodiments.

The inventors recognized that by combining the two methods the respective advantages of the method for providing and receiving a requested medical data record can by synergistically combined.

According to a third embodiment, the invention relates to a computer-implemented method for transmitting a requested medical data record from a selected providing entity to a receiving entity. This method comprises receiving a set of medical data records stored in a database and receiving or initializing a joint data index by the selected providing entity. Furthermore, for each medical data record of the set of medical data records the method comprises applying a plurality of hash functions to a patient identifier corresponding to the medical data record to determine a hash vector, wherein the patient identifier corresponding to the medical data record identifies the patient being subject of the medical data record, and updating the joint data index based on the hash vector, both executed by the selected providing entity. Furthermore, the method comprises transmitting the joint data index from the selected providing entity to the receiving entity.

In an embodiment, the method furthermore comprises receiving a request patient identifier corresponding to the patient and receiving a set of joint data indices by the receiving entity, wherein each joint data index of the joint data indices corresponds to a providing entity from a group of providing entities. The method furthermore comprises determining a hash vector by applying a group of hash functions to the request patient identifier; and determining the selected providing entity of the group of providing entities based on the hash vector and based on the joint data indices.

In an embodiment, the method furthermore comprises transmitting a request for the requested medical data record from the receiving entity to the selected providing entity, wherein the requested medical data record corresponds to a request patient identifier. Optionally, the method comprises verifying the request for the requested medical data record by the selected providing entity. Furthermore, the method comprises transmitting the requested medical data record from the selected providing entity to the receiving entity via a secure communication channel.

In particular, the method for transmitting a requested medical data record is a combination of the method of providing a requested medical data record and the method of receiving a requested medical data record. In particular, the method for transmitting the requested medical data record can comprise all advantageous features of both the methods of providing a requested medical data record and of receiving a requested medical data record.

According to a fourth embodiment, the invention relates to a providing system for providing a requested medical data record to a receiving entity, comprising an interface and a computation unit,
- wherein the interface is configured for receiving a set of medical data records stored in a database;
- wherein the interface or the computation unit is furthermore configured for receiving or initializing a joint data index;
- wherein the computation unit is, for each medical data record of the set of medical data records,
  - configured for applying a plurality of hash functions to a patient identifier corresponding to the medical data record to determine a hash vector, wherein the patient identifier corresponding to the medical data record identifies the patient being subject of the medical data record;
  - and configured for updating the joint data index based on the hash vector;
- wherein the interface is furthermore configured for providing the joint data index to the receiving entity,
- wherein the interface is furthermore configured for receiving a request for the requested medical data record from the receiving entity, wherein the requested medical data record corresponds to a request patient identifier,
- wherein the computation unit is optionally configured for verifying the request for the requested medical data record,
- wherein the interface is furthermore configured for providing the requested medical data record to the receiving entity via a secure communication channel.

In an embodiment, the providing system is configured to execute the previously described method for providing a requested medical data record and its embodiments. The providing system is configured to execute the previously described method for providing a requested medical data record and its embodiments by its interface and its computation unit being configured to execute the respective method steps.

The providing system can be realized as a data processing system or as a part of a data processing system. Such a data processing system can, for example, comprise a cloud-computing system, a computer network, a computer, a tablet computer, a smartphone, a microprocessor or the like. The providing system can comprise hardware and/or software. The hardware can be, for example, a processor system, a memory system and combinations thereof. The hardware can be configurable by the software and/or be operable by the software.

According to a fifth embodiment, the invention relates to a receiving system for receiving a requested medical data record related to a patient from a selected providing entity, comprising an interface and a computation unit,
- wherein the interface is configured for receiving a request patient identifier corresponding to the patient;
- wherein the interface is furthermore configured for receiving a set of joint data indices, wherein each joint data index of the joint data indices corresponds to a providing entity from a group of providing entities;
- wherein the computation unit is configured for determining a hash vector by applying a group of hash functions to the request patient identifier;
- wherein the computation unit is furthermore configured for determining a selected providing entity of the group of providing entities based on the hash vector and based on the joint data indices;
- wherein the interface is furthermore configured for sending a request for the requested medical data record to the selected providing entity;
- wherein the interface is furthermore configured for receiving the requested medical data record from the selected providing entity via a secure communication channel.

In an embodiment, the receiving system is configured to execute the previously described method for receiving a requested medical data record and its embodiments. The receiving system is configured to execute the previously described method for receiving a requested medical data record and its embodiments by its interface and its computation unit being configured to execute the respective method steps.

The receiving system can be realized as a data processing system or as a part of a data processing system. Such a data processing system can, for example, comprise a cloud-computing system, a computer network, a computer, a tablet computer, a smartphone, a microprocessor or the like. The receiving system can comprise hardware and/or software. The hardware can be, for example, a processor system, a memory system and combinations thereof. The hardware can be configurable by the software and/or be operable by the software.

According to a sixth possible embodiment, the invention relates to a transmission system, wherein the transmission system comprises a providing system according to the fourth embodiment of the invention, and wherein the transmission system comprises a receiving system according to the fifth embodiment of the invention. In particular, the transmission system is configured for executing the method for transmitting a requested medical data record. The transmission system is configured for executing the method for transmitting a requested medical data record by the providing system (in particular, by the interface and the computation unit of the providing system) and the receiving system (in particular, by the interface and the computation unit of the receiving system) being configured to executed the respective method steps.

According to a seventh embodiment, the invention relates to a computer program comprising instructions which, when the program is executed by a providing system, cause the providing system to carry out the method for providing a requested medical data record according to the invention and its embodiments; and/or which, when the program is executed by a receiving system, cause the receiving system to carry out the method for receiving a requested medical data record according to the invention and its embodiments.

According to a possible eighth embodiment, the invention relates to a computer program comprising instructions which, when the program is executed by a providing system, cause the providing system to carry out the method for providing a requested medical data record according to the invention and its embodiments.

According to a possible ninth embodiment, the invention relates to a computer program comprising instructions which, when the program is executed by a receiving system, cause the receiving system to carry out the method for receiving a requested medical data record according to the invention and its embodiments.

According to a possible tenth embodiment, the invention relates to a computer program comprising instructions which, when the program is executed by a transmission system, cause the transmission system to carry out the method for transmitting a requested medical data record according to the invention and its embodiments.

According to a eleventh embodiment, the invention relates to a computer-readable medium comprising instructions which, when executed by a providing system, cause the providing system to carry out the method for providing a requested medical data record according to the invention and its embodiments; and/or which, when executed by a receiving system, cause the receiving system to carry out the method for receiving a requested medical data record according to the invention and its embodiments.

According to a possible twelfth embodiment, the invention relates to a computer-readable medium comprising instructions which, when executed by a providing system, cause the providing system to carry out the method for providing a requested medical data record according to the invention and its embodiments.

According to a possible thirteenth embodiment, the invention relates to a computer-readable medium comprising instructions which, when executed by a receiving system, cause the receiving system to carry out the method for receiving a requested medical data record according to the invention and its embodiments.

According to a possible fourteenth embodiment, the invention relates to a computer-readable medium comprising instructions which, when executed by a transmission system, cause the transmission system to carry out the method for transmitting a requested medical data record according to the invention and its embodiments.

The realization of an embodiment of the invention by a computer program product and/or a computer-readable medium has the advantage that already existing providing systems can be easily adopted by software updates in order to work as proposed by embodiments of the invention.

The computer program product can be, for example, a computer program or comprise another element apart from the computer program. This other element can be hardware, for example a memory device, on which the computer program is stored, a hardware key for using the computer program and the like, and/or software, for example a documentation or a software key for using the computer program.

FIG. 1 displays a first embodiment for updating a joint data index $JID.0, \ldots, JID.4$. In this embodiment, the joint data index $JID.0, \ldots, JID.4$ is a Boolean vector (so that all elements can take the values "0"/"false" or "1"/true) with n=8 entries. In this embodiment, a set of three patient identifiers $PID.1, \ldots, PID.3$ is used. In this embodiment, the joint data index $JID.0, \ldots, JID.4$ can be considered as Bloom-Filter.

In this embodiment, m=2 hash functions $h_1, h_2$ are used. Every hash function $h_1, h_2$ takes as input value a patient identifier $PID.1, \ldots, PID.3$ and maps this patient identifier $PID.1, \ldots, PID.3$ to a number between 1 and n=8, corresponding to one of the Boolean elements of a hash vector $HV.1, \ldots, HV.3$. For a general choice of n and k, the elements of the hash vector $HV.1, \ldots, HV.3$ are $(HV.i)=1$, if there is a patient identifier $PID.1, \ldots, PID.3$ with $h_k(PID.i)=j$ (with $j=1, \ldots, n$ and $k=1, \ldots, m$), and 0 otherwise.

The initial joint data index $JID.0$ is initialised with all values equal to "O"/"false". For updating the joint data index $JID.0$ based on the first patient identifier $PID.1$, a first hash vector $HV.1$ is calculated by applying the two hash functions $h_1, h_2$ to the first patient identifier $PID.1$. In this example, $h_1(PID.1)=2$ and $h_2(PID.2)=6$, so that the $2^{nd}$ and the $6^{th}$ element of the first hash vector $HV.1$ are "1", and all the other elements of the first hash vector $HV.1$ are "0". To determine the first joint data index $JID.1$ based on the initial joint data index $JID.0$ and the first hash vector $HV.1$, an element—wise or—composition is calculated by $(JID.1)_j=OR((JID.0)_j, (HV.1)_j)$.

The same procedure is also applied for the other patient identifiers $PID.2, PID.3$. In general, the updated joint data indices $JID.0, \ldots, JID.3$ can be calculated as $(JID.i)_j=OR((JID.(i-1))_j, (HV.i)_j)$.

If the different hash functions $h_1, h_2$ are applied to a patient identifier $PID.1, \ldots, PID.3$, they do not necessarily have to result in two different indices. In this example, $h_1(PID.3)=h_2(PID.3)=4$.

Figure 2:
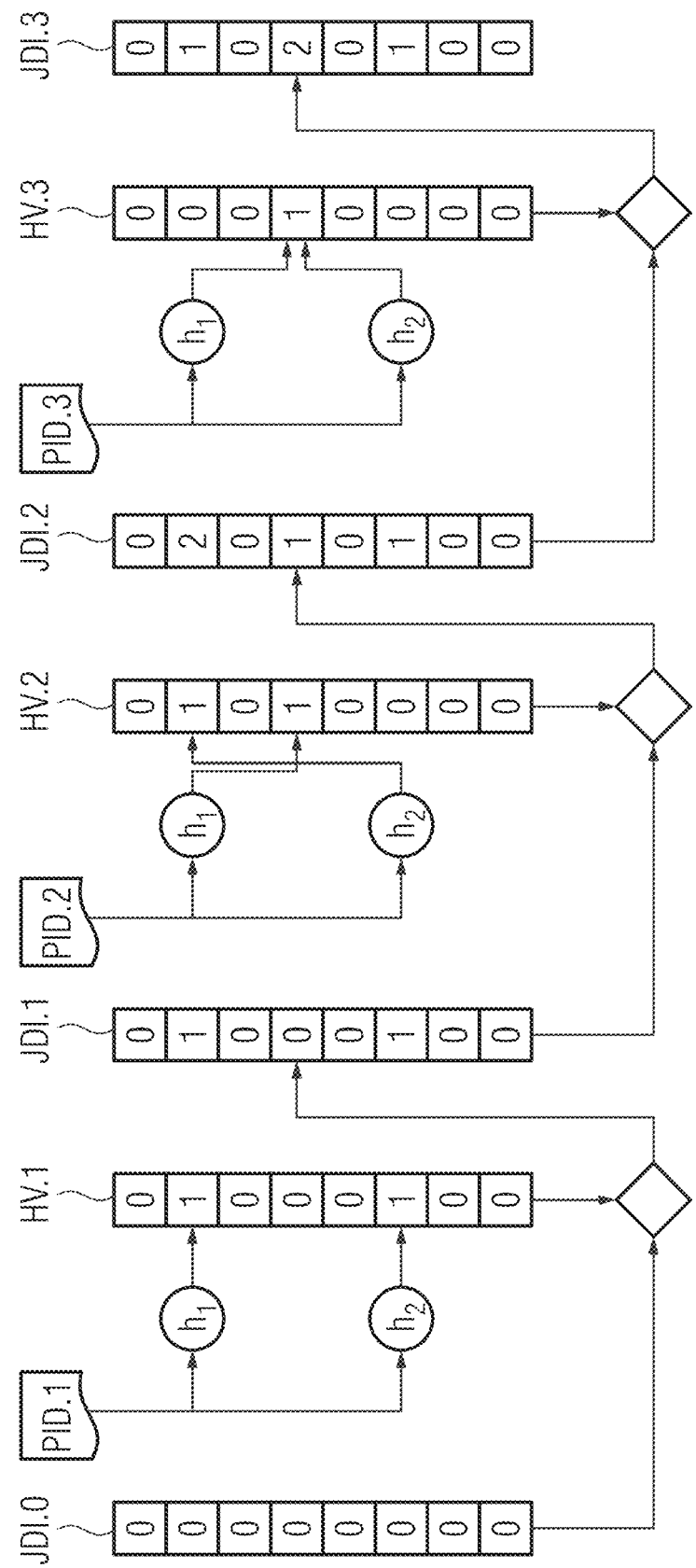
FIG. 2 displays a second embodiment for updating a joint data index.

FIG. 2 displays a second embodiment for updating a joint data index $JID.0, \ldots, JID.4$. In this embodiment, the joint data index $JID.0, \ldots, JID.4$ is an integer vector (so that all elements can take the values 0, 1, 2, . . . ) with n=8 entries. In this embodiment, the joint data index $JID.0, \ldots, JID.4$ can be considered as counting Bloom-Filter.

The calculation of the hash vector $HV.1, \ldots, HV.3$ based on the patient identifier $PID.1, \ldots, PID.3$ is basically identical to the method explained with respect to FIG. 2. However, the updated joint data indices $JID.0, \ldots, JID.3$ are calculated as $(JID.i)_j=(JID.(i-1))_j+(HV.i)_j$, which means that an element of the joint data index $JID.0, \ldots, JID.3$ corresponds to the number of patient identifier $PID.1, \ldots, PID.3$ that are mapped to the element by at least one of the hash functions $h_1, h_2$. In this embodiment, the joint data index $JID.0, \ldots, JID.3$ can be interpreted as a counting Bloom-filter. Using a counting Bloom-filter has the advantage that a patient identifier $PID.1, \ldots, PID.3$ can be removed from the underlying dataset by calculating $(JID.i)=(JID.(i-1))_j-(HV.i)_j$ without recalculating the joint data index $JID.0, \ldots, JID.3$ in its entirety (which is not possible for a non-counting Bloom-filter). However, using a counting Bloom-filter has the disadvantage that the elements of the joint data index $JID.0, \ldots, JID.3$ have integer datatype, and not Boolean datatype, leading to a higher memory consumption for storing and transmitting the joint data index $JID.0, \ldots, JID.3$.

Figure 3:
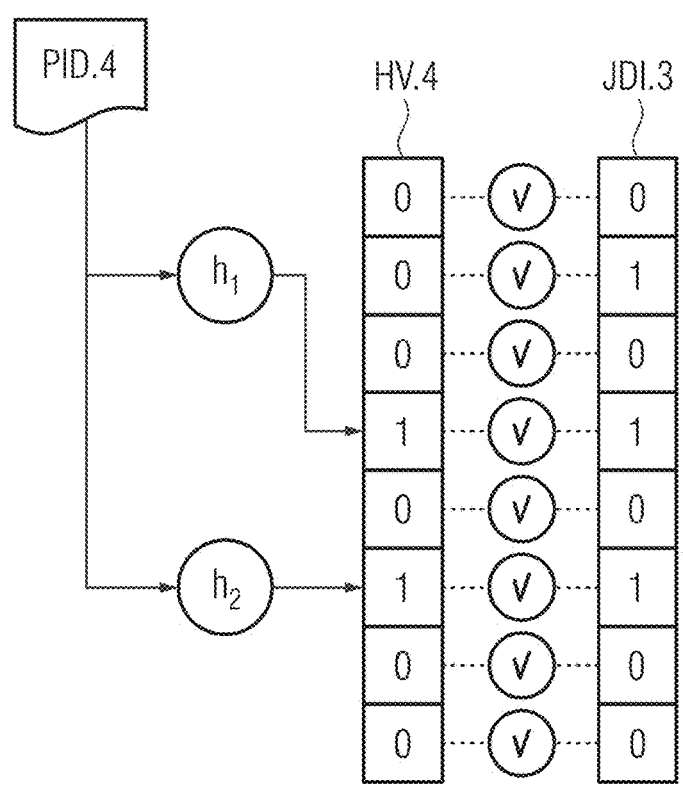
FIG. 3 displays a check of whether a certain patient identifier is potentially contained in the database the joint data index is based on, FIG. 4 displays a check of whether a certain patient identifier is potentially contained in the database the joint data index is based on, FIG. 5 displays the relation between the different entities involved in the methods for providing a requested medical data record and for receiving a requested medical data record, FIG. 6 displays a first embodiment of a data flow diagram corresponding to the method for providing a requested medical data record and/or to the method for receiving a requested medical data record, FIG. 7 displays a second embodiment of a data flow diagram corresponding to the method for providing a requested medical data record and/or to the method for receiving a requested medical data record, FIG. 8 displays a third embodiment of a data flow diagram corresponding to the method for providing a requested medical data record and/or to the method for receiving a requested medical data record, FIG. 9 displays a fourth embodiment of a data flow diagram corresponding to the method for providing a requested medical data record and/or to the method for receiving a requested medical data record, FIG. 10 displays an embodiment of a distributed ledger storing joint data identifiers FIG. 11 displays an embodiment of the method for providing a requested medical data record, FIG. 12 displays another embodiment of the method for providing a requested medical data record, FIG. 13 displays an embodiment of the method for receiving a requested medical data record, FIG. 14 displays a modified embodiment of the method for receiving a requested medical data record, FIG. 15 displays an embodiment of the method for transmitting a requested medical data record, FIG. 16 displays a providing system PSYS and a receiving system RSYS.
Figure 4:
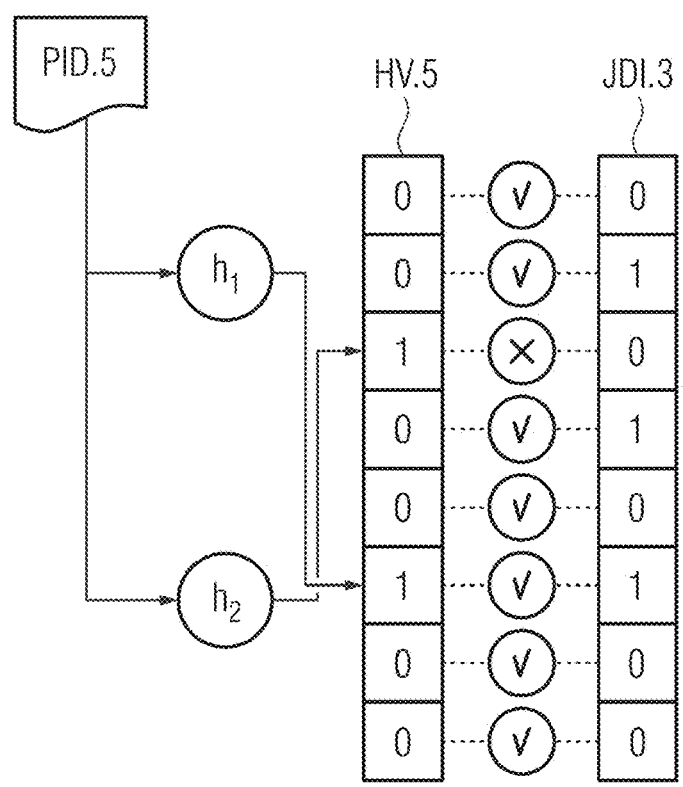

FIG. 3 and FIG. 4 display a check of whether a certain patient identifier $PID.4, PID.5$ is potentially contained in the database $DB.1, \ldots, DB.3$ the joint data index $JID.3$ is based on. For the certain patient identifiers $PID.4, PID.5$ a hash vector $HV.4, HV.5$ is calculated as described with respect to FIG. 1, and the hash vector $HV.4, HV.5$ is compared elementwise with the joint data index $JID.3$.

If for each element with value "1" or "true" in the hash vector $HV.4, HV.5$ the corresponding element of the joint data index $JID.3$ also has the value "1" or "true", the certain patient identifier $PID.4, PID.5$ is potentially contained in the database $DB.1, \ldots, DB.3$ (in this example, this is the case for the certain patient identifier $PID.4$ displayed in FIG. 3). If there is at least one element with value "1" or "true" in the hash vector $HV.4, HV.5$, and the corresponding element of the joint data index $JID.3$ does have a value "0" or "false", the certain patient identifier PID.4, PID.5 is for sure not contained in the database DB.1, ..., DB.3 (in this example, this is the case for the certain patient identifier PID.5 displayed in FIG. 4). Note that there is no matching condition for elements with value "0" or "false" in the hash vector HV.4, HV.5.

The check is slightly different for a counting joint data index JID.3 as displayed in FIG. 2 (but not in FIG. 3 or FIG. 4). If for each element with value 1 in the hash vector HV.4, HV.5 the corresponding element of the joint data index JID.3 also has the value 1 or higher, the certain patient identifier PID.4, PID.5 is potentially contained in the database DB.1, ..., DB.3. If there is at least one element with value 1 in the hash vector HV.4, HV.5, and the corresponding element of the joint data index JID.3 does have a value 0. Note that there is no matching condition for elements with value 0 in the hash vector HV.4, HV.5.

Figure 5:
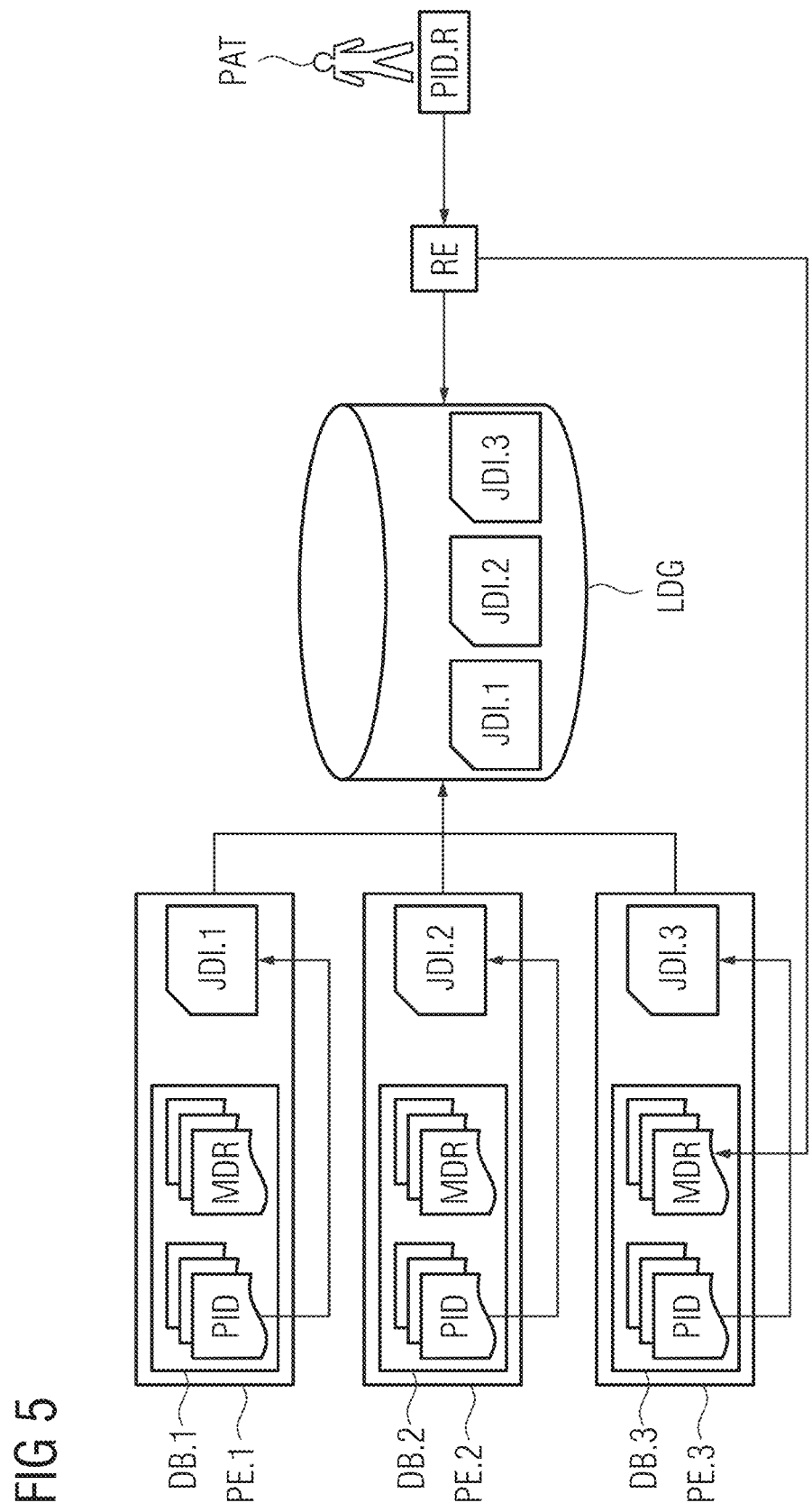

FIG. 5 displays the relation between the different entities involved in the methods for providing a requested medical data record MDR.R and for receiving a requested medical data record MDR.R. In FIG. 5 the situation is displayed for one receiving entity RE. Of course, the methods and systems according to the invention and its embodiments can be used by an arbitrary number of providing entities PE.1, ..., PE.3 and receiving entities RE.

In this embodiment, three different providing entities PE.1, ..., PE.3 are displayed. For example, the first providing entity PE.1 can be a first hospital, the second providing entity PE.2 can be a second hospital different from the first hospital, and the third providing entity PE.3 can be a radiologist's medical practice.

Each of the providing entities PE.1, ..., PE.3 stores a set of medical data records MDR, each of which is related to one of a set of patient identifiers PID which identifies the patient being subject of the respective medical data record. In this embodiment, both the medical data records MDR and the patient identifiers PID are stored in a database DB.1, ..., DB.3 located on the premises of the providing entity PE.1, ..., PE.3.

For each of the providing entities PE.1, ..., PE.3 a joint data index JDI.1, ..., JDI.3 is calculated, which are provided the providing entities to the receiving entities RE. In this embodiment, the joint data indices JDI.1, ..., JDI.3 are provided to the receiving entities RE by documenting the joint data indices JDI.1, ..., JDI.3 within a distributed ledger. Alternatively, the joint data indices JDI.1, ..., JDI.3 can also be stored within a webserver that can be accessed by the receiving entities.

Consider now a situation that a patient PAT is subject of a medical diagnosis or a medical therapy by a receiving entity RE (e.g. the general practitioner of the patient PAT), which needs the medical history of the patient PAT which might be distributed in the databases DB.1, ..., DB.3 of the providing entities PE.1, ..., PE.3 inaccessible by the receiving entity RE. The receiving entity RE now checks based on the request patient identifier PID.R (which is the patient identifier of the patient PAT, e.g., its social insurance number) and based on the joint data indices JID.1, ..., JID.3 whether there is the possibility that the corresponding providing entity PE.1, ..., PE.3 stores a requested medical data record MDR.R the patient PAT is subject of, and selects the providing entity PE.1, ..., PE.3 that possibly store the requested medical data record MDR.R as selected providing entity PE.S. In this embodiment, only the third providing entity PE.3 possibly stored the requested medical data record MDR.R, so the receiving entity RE gets in contact only with the third providing entity PE.3 as selected providing entity PE.S in order to receive the requested medical data record MDR.R. Of course, it is also possible that none of the providing entities PE.1, ..., PE.3 is selected, or that more than one of the providing entities PE.1, ..., PE.3 is selected.

Figure 6:
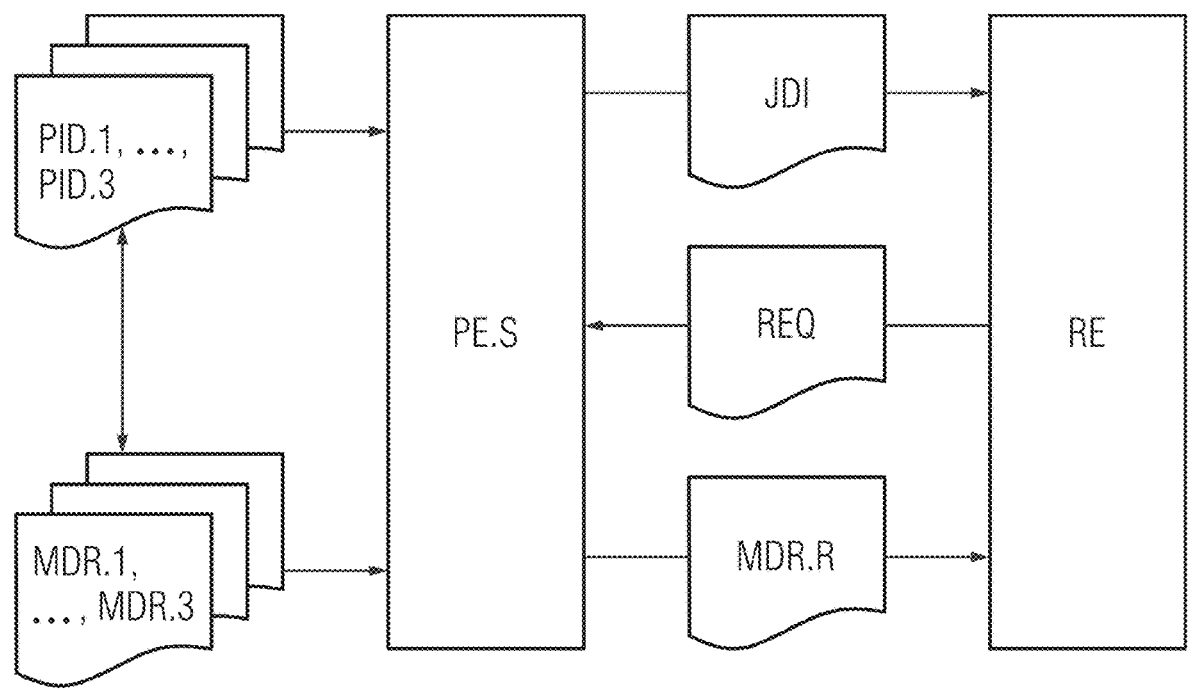

FIG. 6 shows a first embodiment of a data flow diagram corresponding to the method for providing a joint data identifier JID and/or to the method for receiving a requested medical data record MDR.R.

In this embodiment, the (selected) providing entity PE.S creates a joint data index JDI based on patient identifiers PID.1, ..., PID.3 corresponding to medical data records MDR.1, ..., MDR.3 stored in a database DB.1, ..., DB.3 (not displayed in FIG. 6).

After having determined that a requested medical data record MDR.R corresponding to the patient PAT (in particular, the request patient identifier PID.R of the patient PAT) is potentially stored by the selected providing entity PE.S, a request REQ is transmitted from the requesting entity RE to the selected providing entity PE.S.

Having successfully determined that the requested medical data record MDR.R is in fact stored in the database DB.1, ..., DB.3, the selected providing entity PE.S provides the requested medical data record MDR.R to the receiving entity MDR.

Figure 7:
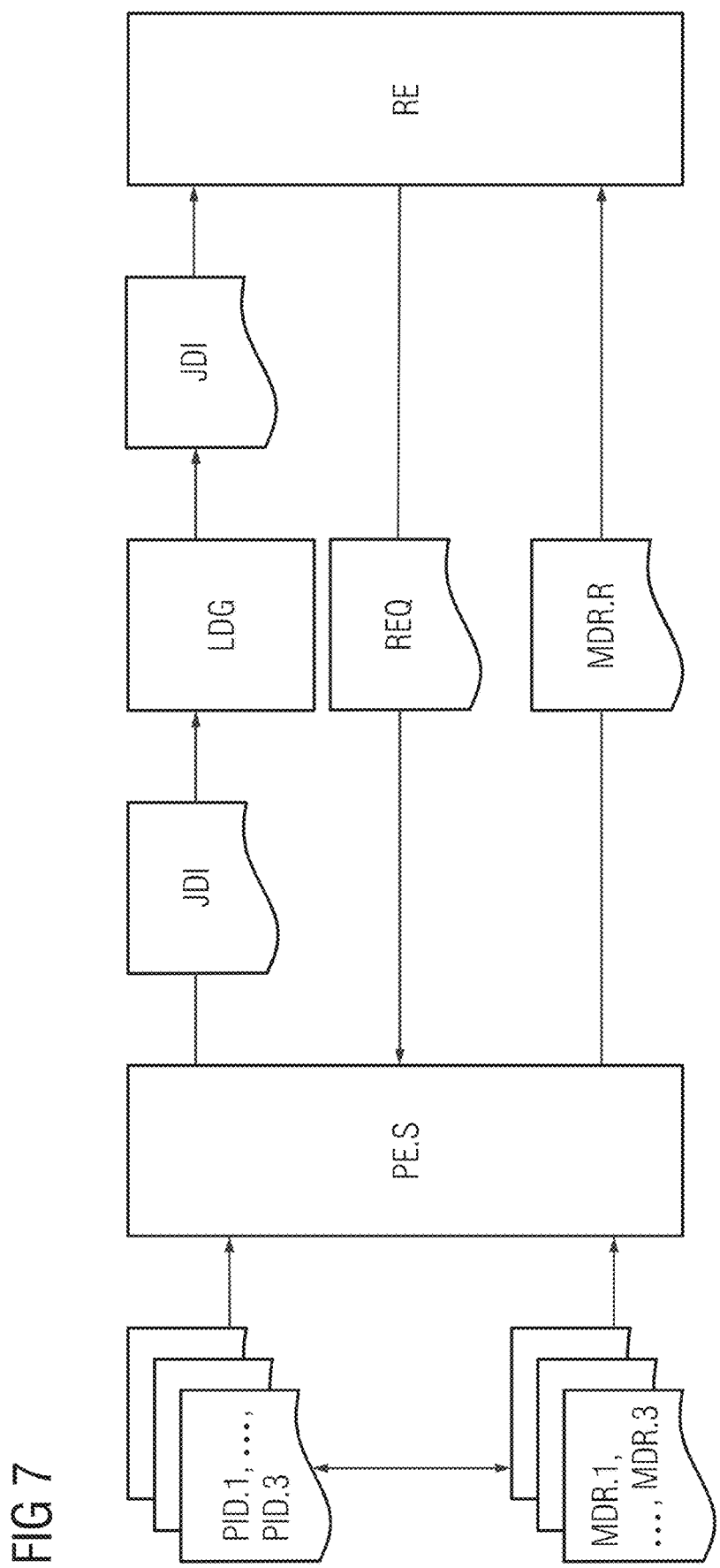

FIG. 7 shows a second embodiment of a data flow diagram corresponding to the method for providing a joint data identifier JID and/or to the method for receiving a requested medical data record MDR.R. The data transferred between the selected providing entity PE.S and the receiving entity RE in the second embodiment is equivalent with the first embodiment, with the exception of the joint data identifier JDI.

In this second embodiment, the joint data identifier JDI is transmitted from the providing entity PE.S to the receiving entity RE by the selected providing entity PE.S documenting the joint data identifier JDI in a distributed ledger LDG (preferably, the joint data identifier JDS is documented together with an identifier of the selected providing entity PE.S to be able to determine which joint identifier JDS in the distributed ledger LDG corresponds to which providing entity PE.1, ..., PE.3, PE.S). Furthermore, the receiving entity RE receives the joint data identifier JDI by reading and/or accessing the distributed ledger LDG.

Figure 8:
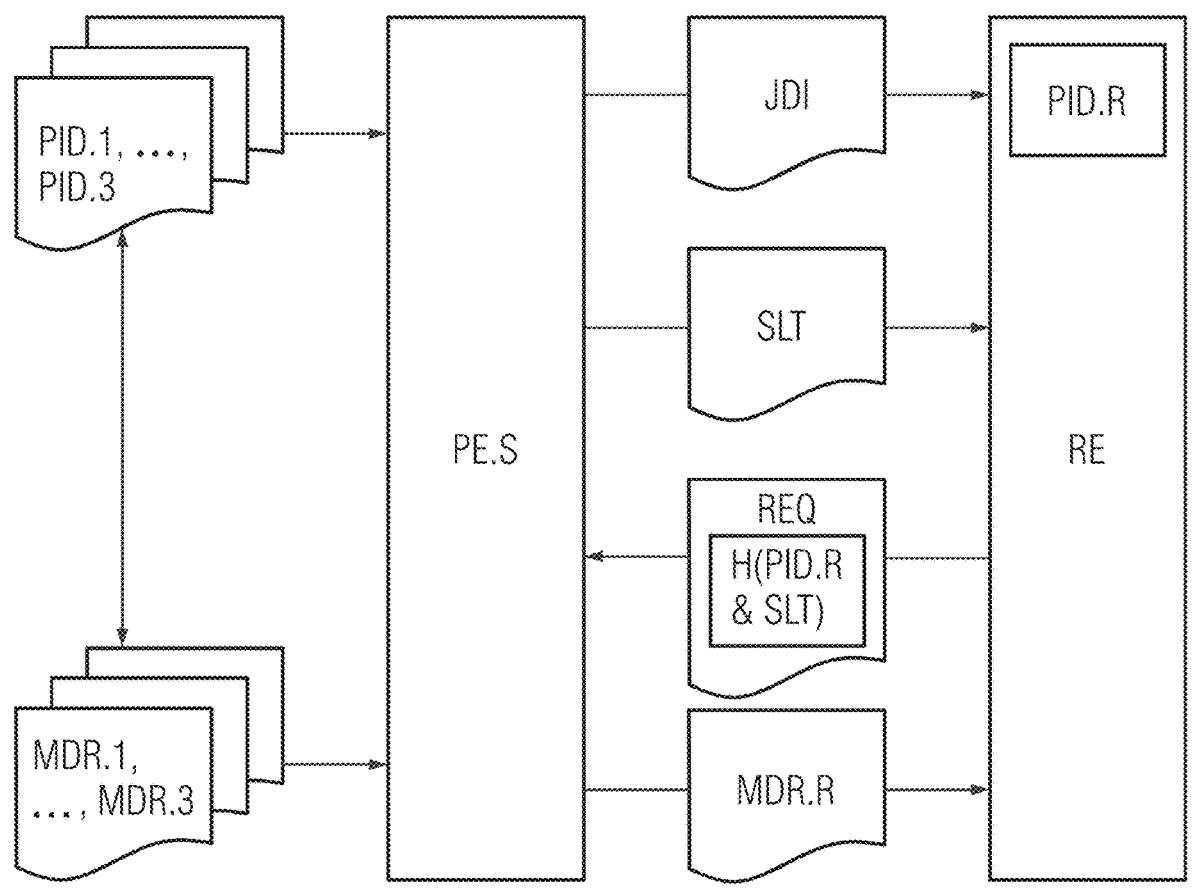
Figure 9:
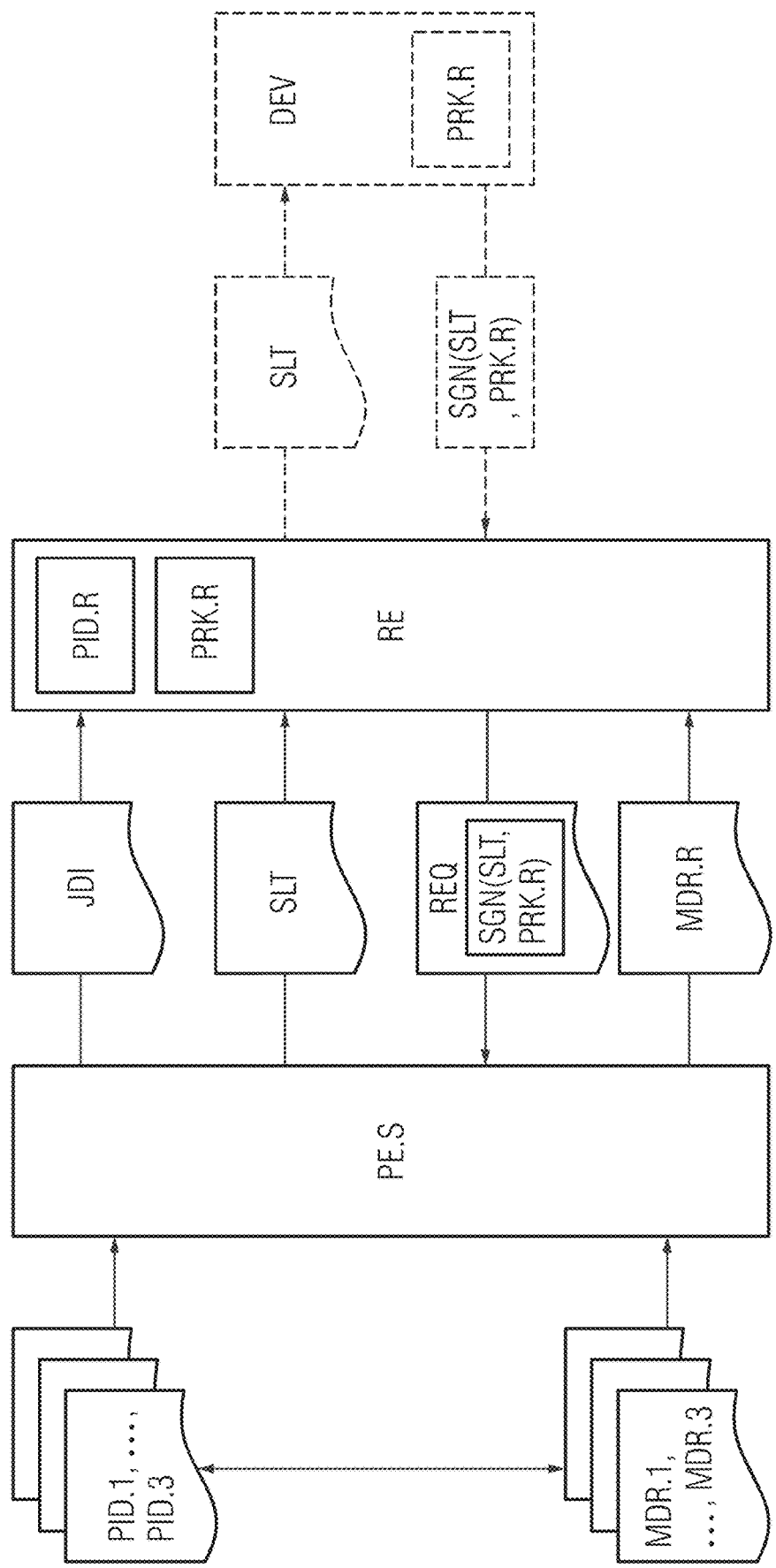

FIG. 8 and FIG. 9 show a third and a fourth embodiment of a data flow diagram corresponding to the method for providing a joint data identifier JID and/or to the method for receiving a requested medical data record MDR.R. The data transferred between the selected providing entity PE.S and the receiving entity RE in the third and fourth embodiment is equivalent with the first embodiment, with the exception of a salt SLT as well as with the exception of the details with respect to the request REQ.

In the third embodiment, a salt SLT is created by the selected providing entity PE.S (e.g. by way of a random number generator), and then transmitted from the selected providing entity PE.S to the receiving entity RE. The receiving entity than calculates a salted hash H(PID.R & SLT) of the request patient identifier PID.R, which is a hash of a combination of the request patient identifier PID.R and the salt SLT. The salted hash H(PID.R & SLT) is then a part of the request REQ transmitted from the receiving entity RE to the selected providing entity PE.S.

Verifying VRF-REQ the request REQ by the selected providing entity PE.S then comprises computing the salted hash of request patient identifier PID.R contained in the database DB.1, ..., DB.3 and comparing the computed salted hash with the received salted hash H(PID.R & SLT). By transmitting a hash of the request patient identifier PID.R the selected providing entity PE.S does not gain access to the request patient identifier PID.R in the case that there is no medical data record MDR.1, . . . , MDR.3 related to the request patient identifier PID.R stored in the database DB.1, . . . , DB.3. Using a salted hash H(PID.R & SLT) ensures that no metadata correlation can be used analyzing the hashes of the request patient identifier PID.R transmitted between the different entities.

In the fourth embodiment, a salt SLT is created by the selected providing entity PE.S (e.g. by way of a random number generator), and then transmitted from the selected providing entity PE.S to the receiving entity RE. The receiving entity than calculates a signature SGN(SLT, PRK.R) of the salt, signed with a private key PRK.R corresponding to a public key related to the request patient identifier PID.R. In particular, the request patient identifier PID.R is the public key corresponding to the private key PRK.R. The signature SGN(SLT, PRK.R) is then a part of the request REQ transmitted from the receiving entity RE to the selected providing entity PE.S.

Verifying VRF-REQ the request REQ by the selected providing entity PE.S then comprises verifying the signature using the public key corresponding to the private key PRK.R, in particular using the request patient identifier PID.R contained in the database DB.1, . . . , DB.3. By transmitting a signature signed with the private key PRK.R corresponding to the requested private identifier PID.R an authorization of the requesting entity RE to access the requested medical data record MDR.R can be checked. In this case, only a receiving entity in possession of the private key PRK.R can access the requested medical data record MDR.R.

In the displayed third embodiment, the private key PRK.R is stored by the receiving entity RE. Alternatively (and displayed by dashed lines), the private key PRK.R can be a patient-specific private key PRK.R, stored on a device DEV (e.g., a smartphone) of the patient PAT. In this case, the salt SLT can be forwarded from the receiving entity RE to the device DEV of the patient PAT, which calculates the signature SGN(SLT, PRK.R) and sends it back to the receiving entity RE. The transmitting between the device DEV of the patient PAT and the receiving entity RE can be done via a data network (e.g. Bluetooth or Wi-Fi), or by using QR-codes displayed on the respective displays and recognized by a camera of the other device or entity.

Optionally, within the third and the fourth embodiment, the joint data index JDI can be transmitted from the selected providing entity PE.S to the receiving entity RE by way of the distributed ledger LDG as described with respect to the second embodiment.

Optionally, there can be an embodiment where both the salted hash H(PID.R & SLT) as in the third embodiment and the signature SGN(SLT, PRK.R) as in the fourth embodiment are used.

Figure 10:
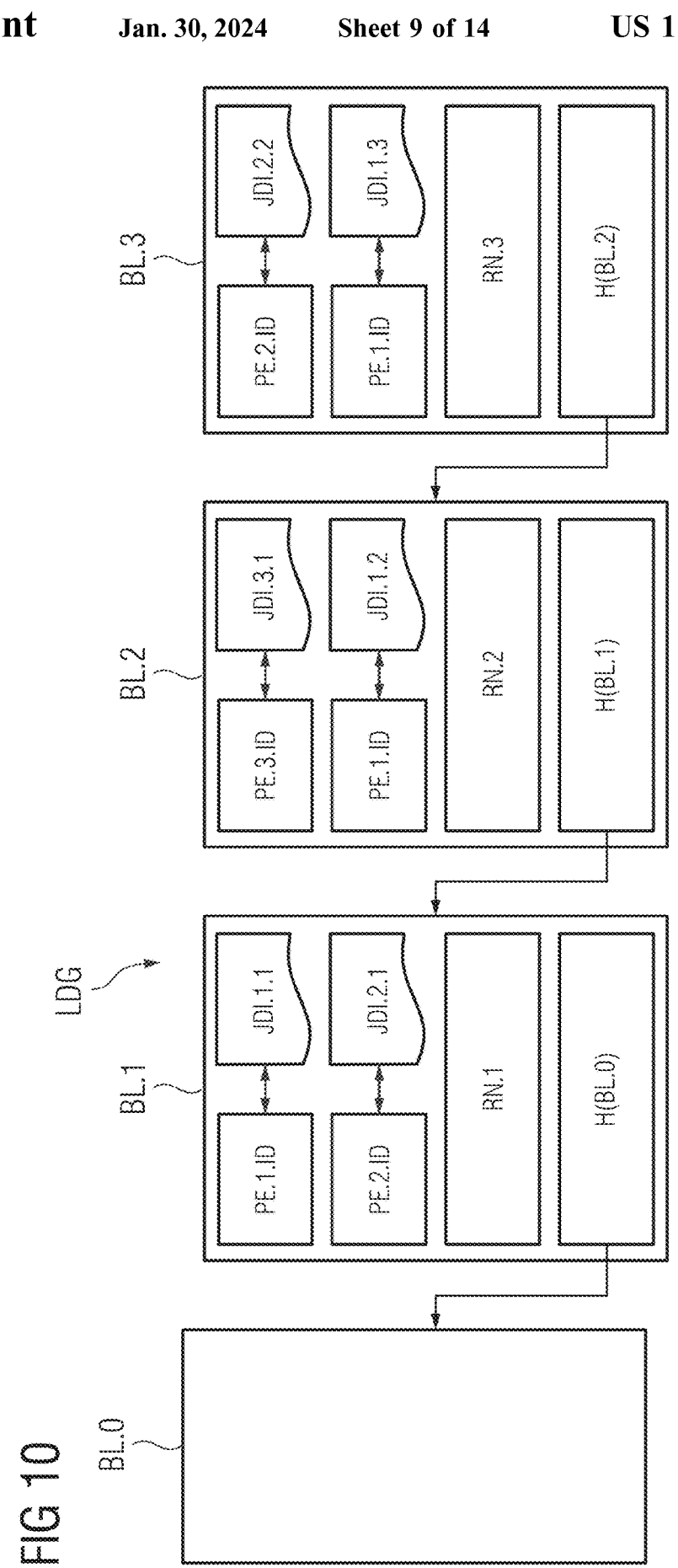

FIG. 10 displays an embodiment of a distributed ledger LDG storing joint data identifiers JDI.1.1, JDI.1.2, JDI.1.3, JDI.2.1, JDI.2.2, JDI.3.1.

The distributed ledger LDG comprises data blocks BL.0, BL.1, BL.2, BL.3 wherein each of the data blocks BL.0, . . . , BL.3 is linked to another data block BL.0, . . . , BL.3 (in this embodiment, the data block BL.0 is linked to a data block which is not displayed). A link between two data blocks BL.0, BL.3 is a directional information, this means that for each link there is a well-defined start of the link and a well-defined end of the link. In particular, if a first data block BL.0, . . . , BL.3 is linked to a second data block BL.0, . . . , BL.3, this means that the first data block BL.0, . . . , BL.3 is the start of the link and the second data block BL.0, . . . , BL.3 is the end of the link. In other words, a first data block BL.0, . . . , BL.3 being linked to a second data block BL.0, . . . , BL.3 does not imply that the second data block BL.0, . . . , BL.3 is linked to the first data block BL.0, . . . , BL.3.

In this embodiment, each data block BL.0, . . . , BL.3 is linked to exactly one other data block BL.0, . . . , BL.3. Alternatively, a data block BL.0, . . . , BL.3 can be linked to several other data blocks BL.0, . . . , BL.3. In particular, each data block BL.0, . . . , BL.3 can be linked to a fixed number of other data blocks BL.0, . . . , BL.3. A data block BL.0, . . . , BL.3 can also be linked to itself.

In this embodiment, a first data block BL.0, . . . , BL.3 is linked to a second data block BL.0, . . . , BL.3 by the first data block BL.0, . . . , BL.3 comprising a hash H(BL.0), . . . , H(BL.2) of the second data block BL.0, . . . , BL.3. In particular, the hash H(BL.0), . . . , H(BL.2) of a data block BL.0, . . . , BL.3 can be calculated with a hash function not contained in the plurality of hash functions h1, h2 used for calculating a joint data index JDI.1.1, JDI.1.2, JDI.1.3, JDI.2.1, JDI.2.2, JDI.3.1. Alternatively, other link information can be included into the first data block BL.0, . . . , BL.3 to indicate that it is linked to the second data block BL.0, . . . , BL.3. In this embodiment, the H(BL.0), . . . , H(BL.2) is the result of the application of the SHA256 hash function on the second data block BL.0, . . . , BL.3. In particular, the SHA256 hash function is applied to a concatenation of the contents of the second data block BL.0, . . . , BL.3. In particular, for inserting a data block BL.0, . . . , BL.3 into the distributed ledger LDG, a consensus algorithm (e.g. proof of work, proof of storage, proof of stake, proof of elapsed time) must be executed, wherein the consensus algorithm may be based on choosing the nonce RN.1, RN.2, RN.3 of the data block BL.0, . . . , BL.3 to be inserted. In this embodiment, the nonce RN.1, RN.2, RN.3 must be chosen by the creator of the data block BL.0, . . . , BL.3 such that the hash H(TSB.1), . . . , H(TSB.3), H(FTSB) of the data block BL.0, . . . , BL.3 fulfills a certain condition. In this embodiment, the condition is that the hash H(TSB.1), . . . , H(TSB.3), H(FTSB) of the data block BL.0, . . . , BL.3 is smaller than a given threshold.

In this embodiment, each data block BL.0, . . . , BL.3 comprises one or more pairs of identifiers PE.1.ID, . . . , PE.3.ID identifying providing entity PE.1, . . . , PE.3 and corresponding joint data identifiers JDI.1.1, JDI.1.2, JDI.1.3, JDI.2.1, JDI.2.2, JDI.3.1. The number of pairs in each data block BL.0, . . . , BL.3 is not necessarily constant, so that there can be data blocks with a different number of pairs. In particular, for each data block BL.0, . . . , BL.3, there is only one pair comprising a certain identifier PE.1.ID, . . . , PE.3.ID identifying one providing entity PE.1, . . . , PE.3.

An identifier PE.1.ID, . . . , PE.3.ID identifying providing entity PE.1, . . . , PE.3 can for example be an IP (acronym for "Internet Protocol") address of a server of the respective providing entity PE.1, . . . , PE.3, or a URL (acronym for "Universal Resource Locator") corresponding to the respective providing entity PE.1, . . . , PE.3.

In this embodiment, documenting a joint data identifier JDI.1.1, JDI.1.2, JDI.1.3, JDI.2.1, JDI.2.2, JDI.3.1 in a distributed ledger corresponds to creating a block comprising a pair comprising the joint data identifier JDI.1.1, JDI.1.2, JDI.1.3, JDI.2.1, JDI.2.2, JDI.3.1 and the identifier PE.1.ID, . . . , PE.3.ID identifying the providing entity PE.1, ..., PE.3 the joint data identifier JDI.1.1, JDI.1.2, JDI.1.3, JDI.2.1, JDI.2.2, JDI.3.1 corresponds to.

If the joint data identifier JDI.1.1, JDI.1.2, JDI.1.3, JDI.2.1, JDI.2.2, JDI.3.1 corresponding to a providing entity PE.1, ..., PE.3 has to be updated, because additional medical data records MDR.1, ..., MDR.3 corresponding to additional patient identifiers PID.1, ..., PID.3 are stored in the corresponding database DB.1, ..., DB.3, a new data block BL.0, ..., BL.3 comprising the updated joint data identifier JDI.1.1, JDI.1.2, JDI.1.3, JDI.2.1, JDI.2.2, JDI.3.1 has to be created.

For example, in this embodiment the block BL.1 comprises the pair of an identifier PE.1.ID of a first providing entity PE.1 and a first version of the joint data index JDI.1.1 corresponding to the first providing entity PE.1. This situation can be interpreted that at the time of the creation of the data block BL.1 the joint data index JDI.1.1 of the patient identifiers PID.1, ..., PID.3 being stored in the database DB.1 of the first providing entity PE.1 was equivalent to the joint data index JDI.1.1 stored in the data block BL.1.

If a second version of the joint data index JDI.1.2 or a third version of the joint data index JDI.1.3 have to be created corresponding to the first providing entity PE.1, because additional medical data records MDR.1, ..., MDR.3 are included into the database DB.1, a pair comprising the identifier PE.1.ID of the first providing entity PE.1 and the second version of the joint data index JDI.1.2 or the third version of the joint data index JDI.1.3 have to be stored in additional data blocks BL.2, BL.3. This is because in a distributed ledger LDG it is almost impossible to change data blocks BL.0, ..., BL.3 which are not one of the last few data blocks BL.0, ..., BL.3 in the distributed ledger LDG.

As a consequence, for receiving the current version of the joint data identifier JDI.1.1, JDI.1.2, JDI.1.3, JDI.2.1, JDI.2.2, JDI.3.1, the distributed ledger LDG has to be scanned starting from the latest data block BL.0, ..., BL.3, and the version of the joint data identifier JDI.1.1, JDI.1.2, JDI.1.3, JDI.2.1, JDI.2.2, JDI.3.1 corresponding to the first occurrence of the identifier PE.1.ID, ..., PE.3.ID of the corresponding providing entity PE.1, ..., PE.3 corresponds to the current version of the joint data identifier JDI.1.1, JDI.1.2, JDI.1.3, JDI.2.1, JDI.2.2, JDI.3.1.

Alternatively, the distributed ledger LDG can also comprise data blocks which are not related to joint data identifier JDI.1.1, JDI.1.2, JDI.1.3, JDI.2.1, JDI.2.2, JDI.3.1 or do not contain a joint data identifier JDI.1.1, JDI.1.2, JDI.1.3, JDI.2.1, JDI.2.2, JDI.3.1. For example, the data blocks BL.0, ..., BL.3 documenting joint data identifier JDI.1.1, JDI.1.2, JDI.1.3, JDI.2.1, JDI.2.2, JDI.3.1 can be embedded into a distributed ledger LDG storing other data, e.g. within the Bitcoin blockchain or the Ethereum blockchain. In this case, data blocks BL.0, ..., BL.3 can also be linked to other data blocks and vice versa.

Figure 11:
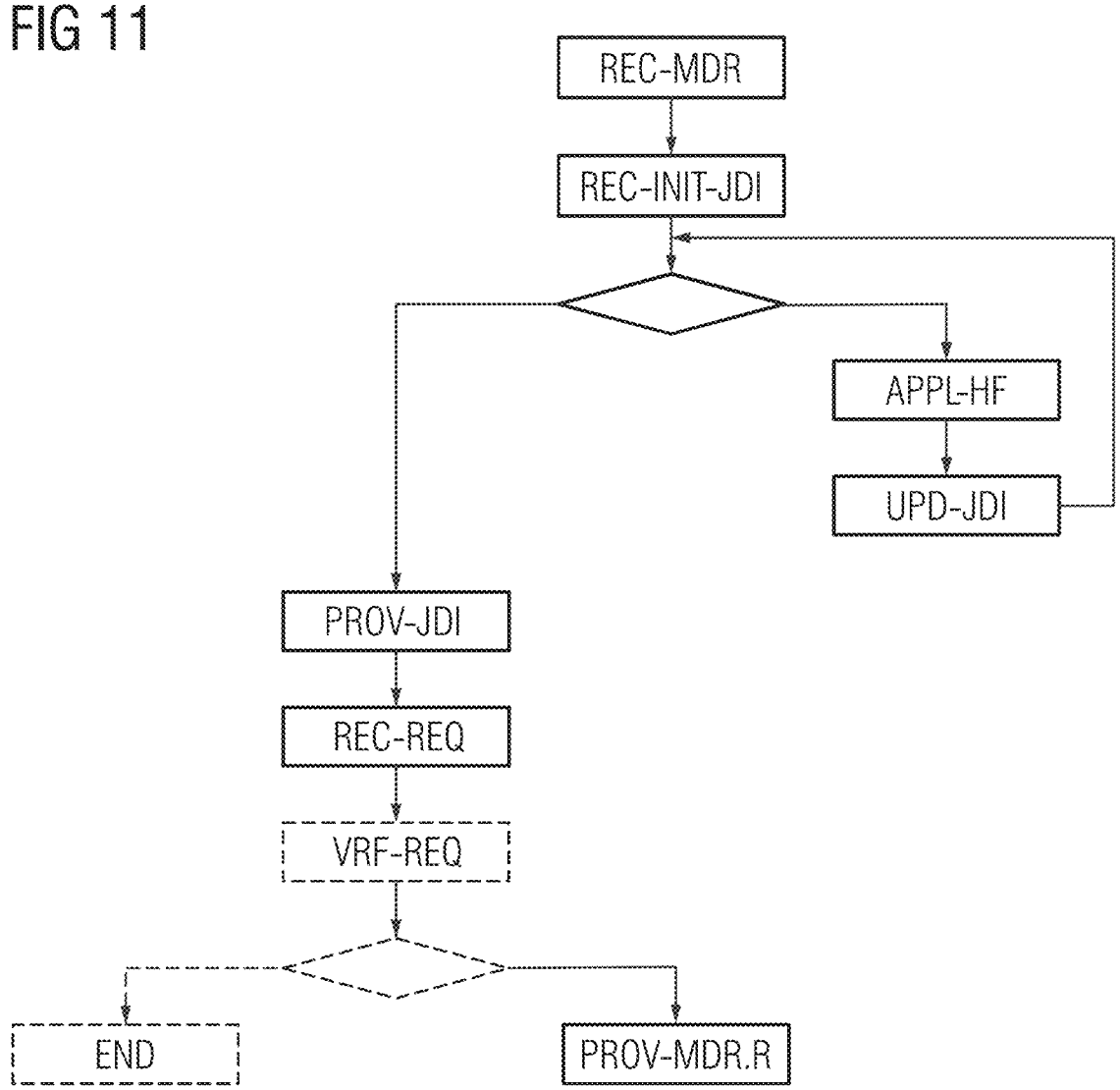
Figure 12:
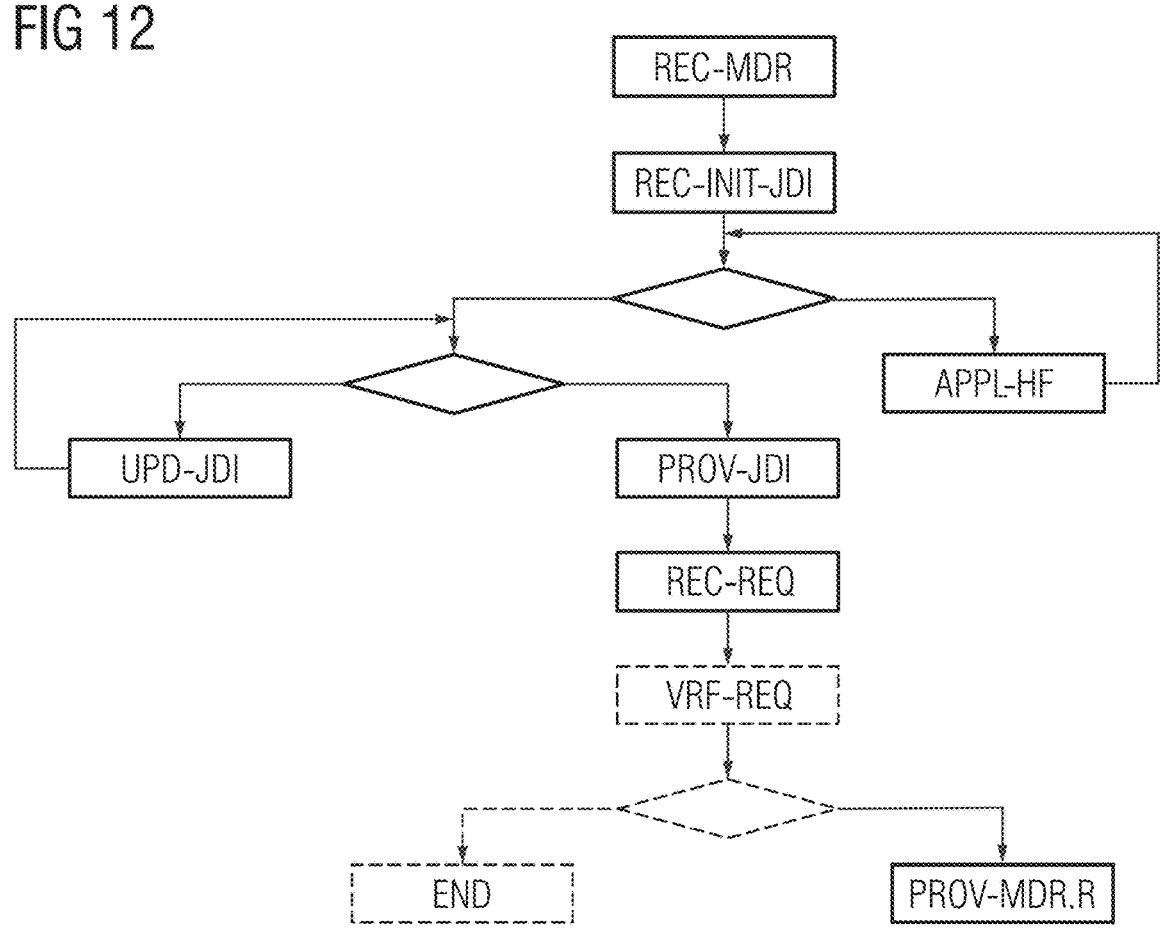

FIG. 11 and FIG. 12 display flow charts of embodiments of the method for providing a requested medical data record MDR.R to a receiving entity RE.

The first step of the displayed embodiments is receiving REC-MDR a set of medical data records MDR.1, ..., MDR.3 stored in a database DB.1, ..., DB.3 by an interface of a providing system PSYS.

In these embodiments, the database DB.1, ..., DB.3 is a PACS (acronym for "Picture Archiving and Communication System") of a hospital storing imaging data, in particular computed tomography or magnetic resonance images. Other examples for databases DB.1, ..., DB.3 are HIS (acronym for "hospital information system"), LIS (acronym for "laboratory information system") or RIS (acronym for "radiology information system"). For each providing entity PE, there can be several databases DB.1, ..., DB.3 to store medical data records MDR.1, ..., MDR.3.

The database DB.1, ..., DB.3 may be located within the providing entity PE, in particular, the database DB.1, ..., DB.3 may be accessible only by information technology equipment of the providing entity PE or in the private network (another term is "intranet") of the providing entity PE. Alternatively, the database DB.1, ..., DB.3 can be located outside of the premises of the providing entity PE, in particular, the database DB.1, ..., DB.3 can be a cloud database hosted by a cloud provider.

Each of the medical data records MDR.1, ..., MDR.3 is the medical data record MDR.1, ..., MDR.3 of a patient PAT. In particular, for each of the medical data records MDR.1, ..., MDR.3 there is a patient identifier PID.1, ..., PID.3 identifying the patient PAT being subject of the medical data record MDR.1, ..., MDR.3. There can be several medical data records MDR.1, ..., MDR.3 for a single patient PAT in the database DB.1, ..., DB.3, each then corresponding to the same patient identifier PID.1, ..., PID.3. For example, in this embodiment, there can be several DICOM (acronym for "Digital Imaging and Communication") studies corresponding to the same patient PAT stored in the PACS, each of these studies can be interpreted as a single medical data record MDR.1, ..., MDR.3. Alternatively, for each patient PAT there is only one medical data record MDR.1, ..., MDR.3 storing all information available to the providing entity PE with respect to a certain patient PAT. An example for such a medical data record MDR.1, ..., MDR.3 is an EMR or EHR (acronym for "electronic medical record" or "electronic health record").

In these embodiments, the patient identifier PID.1, ..., PID.3 has a standardized format, being a number uniquely assigned to a patient (e.g. the social insurance number or the number of an official document of the patient). Furthermore, in this embodiment, the patient identifier PID.1, ..., PID.3 is a part of the medical data record MDR.1, ..., MDR.3, in particular, the patient identifier PID.1, ..., PID.3 can be contained in the metadata of the medical data record MDR.1, ..., MDR.3. Alternatively, the patient identifier PID.1, ..., PID.3 can be stored in relation to the respective medical data record MDR.1, ..., MDR.3, e.g., there can be a data structure (e.g. a table in the database DB.1, ..., DB.3) storing pairs of medical data records MDR.1, ..., MDR.3 or identifiers of medical data records MDR.1, ..., MDR.3 and the respective patient identifiers PID.1, ..., PID.3

The second step of the displayed embodiments is receiving or initializing REC-INIT-JDI a joint data index JDI.0, ..., JDI.4. In this embodiment, the joint data index JDI.0, ..., JDI.4 is a Bloom filter or a counting Bloom filter, in particular a Bloom filter or a counting Bloom filter indicative of the patient identifiers PID.1, ..., PID.3 corresponding to the medical data records MDR.1, ..., MDR.3 stored in the database DB.1, ..., DB.3 that are not contained in the set of medical data records MDR.1, ..., MDR.3 received in the step of receiving REC-MDR the set of medical data records MDR.1, ..., MDR.3.

In particular, the set of medical data records MDR.1, MDR.3 can comprise all medical data records MDR.1, ..., MDR.3 stored in the database DB.1, ..., DB.3. In this case, receiving REC-JDI the joint data index JDI.0, ..., JDI.4 is equivalent with initializing the joint data index JDI.0, ..., JDI.4. If the joint data index JDI.0, ..., JDI.4 is a Bloom filter, initializing the joint data index JDI.0, . . . , JDI.4 is equivalent to assign the value "False" or "0" to every element of the joint data index JDI.0, . . . , JDI.4. If the joint data index JDI.0, . . . , JDI.4 is a counting Bloom filter, initializing the joint data index JDI.0, . . . , JDI.4 is equivalent to assign the integer value "0" to every element of the joint data index JDI.0, . . . , JDI.4.

As next steps, for each medical data record MDR.1, . . . , MDR.3 of the set of medical data records MDR.1, . . . , MDR.3 the steps of applying APPL-HF a plurality of hash functions h1, h2 to a patient identifier PID.1, . . . , PID.3 corresponding to the medical data record MDR.1, . . . , MDR.3 to determine a hash vector HV.1, . . . , HV.3, wherein the patient identifier PID.1, PID.3 corresponding to the medical data record MDR.1, . . . , MDR.3 identifies the patient being subject of the medical data record MDR.1, . . . , MDR.3, and of updating UPD-JDI the joint data index JDI.0, . . . , JDI.4 based on the hash vector HV.1, . . . , HV.3 are executed.

In the flow charts of FIG. 11 and FIG. 12, the loop over all medical data record MDR.1, . . . , MDR.3 of the set of medical data records MDR.1, . . . , MDR.3 is indicated by the rhombus representing a conditional statement. If the condition that all medical data records MDR.1, . . . , MDR.3 of the set of medical data records MDR.1, . . . , MDR.3 have been processed is not fulfilled, the step of applying APPL-HF a plurality of hash functions h1, h2 and/or the step of updating UPD-JDI the joint data index JDI.0, . . . , JDI.4 are executed for a nonprocessed medical data records MDR.1, . . . , MDR.3, otherwise the flowchart continues with the other branch.

In the first embodiment displayed in FIG. 11, for each medical data record MDR.1, . . . , MDR.3 the step of applying APPL-HF a plurality of hash functions h1, h2 and the step of updating UPD-JDI the joint data index JDI.0, . . . , JDI.4 are executed in sequence, before continuing with the next medical data record MDR.1, . . . , MDR.3. In the second embodiment displayed in FIG. 13a, the step of applying APPL-HF a plurality of hash functions h1, h2 is first executed for all medical data records MDR.1, . . . , MDR.3, before the step of updating UPD-JDI the joint data index JDI.0, . . . , JDI.4 is executed for all medical data records MDR.1, . . . , MDR.3 afterwards. Alternatively, there can be a processing sequence mixed between the displayed first and second embodiment. In particular, the steps of applying APPL-HF a plurality of hash functions h1, h2 and the step of updating UPD-JDI the joint data index JDI.0, . . . , JDI.4 can be executed in parallel for different medical data records MDR.1, . . . , MDR.3 of the set of medical data records MDR.1, . . . , MDR.3.

In these embodiments, the applying APPL-HF of the plurality of hash functions h1, h2 and the updating UPD-JDI the joint data index JDI.0, . . . , JDI.4 is executed according to the detailed description of FIG. 1 (for the joint data index JDI.0, . . . , JDI.4 being a Bloom filter) or according to the detailed description of FIG. 2 (for the joint data index JDI.0, JDI.4 being a counting Bloom filter).

The next step of the displayed embodiments is providing PROV-JDI the joint data index JDI.0, . . . , JDI.4 to the receiving entity RE with the interface PSYS.IF of the providing system PSYS.

In these embodiments, the joint data index JDI.0, . . . , JDI.4 is documented in a distributed ledger LDG. The distributed ledger is a blockchain, but of course it is possible to use other types of distributed ledgers without modifying the remaining process. Alternatively, the joint data index JDI.0, JDI.4 can be directly provided to the receiving entity RE by way of a network (e.g. using an E-Mail or other device(s) of direct communication), or by publishing the joint data index JDI.0, . . . , JDI.4 (e.g. by a webserver operated by the selected providing entity PE, or by a webserver operated by a third entity being different from the providing entity PE and the receiving entity RE).

The next step of the displayed embodiments is receiving REC-REQ a request REQ for the requested medical data record MDR.R from the receiving entity RE with the interface PSYS.IF of the providing system PSYS, wherein the requested medical data record MDR.R corresponds to a request patient identifier PID.R. The request patient identifier PID.R is a patient identifier of a patient PAT being subject of the requested medical data record MDR.R.

In these embodiments, the request REQ comprises a salted hash H(PID.R & SLT) of the request patient identifier PID.R and a signature SGN(SLT, PRK.R) signed with a private key PRK.R related to the request patient identifier PID.R. Alternatively, the request REQ can comprise a salted hash H(PID.R & SLT) of the request patient identifier PID.R, but no signature SGN(SLT, PRK.R) signed with the private key PRK.R related to the request patient identifier PID.R. Alternatively, the request REQ can comprise a signature SGN(SLT, PRK.R) signed with the private key PRK.R related to the request patient identifier PID.R, but no salted hash of the request patient identifier PID.R. Alternatively, the request REQ can neither comprise a salted hash H(PID.R & SLT) of the request patient identifier PID.R nor a signature SGN(SLT, PRK.R) signed with a private key PRK.R related to the request patient identifier PID.R. A method for creating and exchanging the salted hash H(PID.R & SLT) of the request patient identifier PID.R is explained with respect to FIG. 8, a method for creating an exchanging the signature SGN(SLT, PRK.R) signed with the private key PRK.R related to the request patient identifier PID.R is explained with respect to FIG. 9. Alternatively to the salted hash H(PID.R & SLT) of the request patient identifier PID.R, the request REQ can also comprise the request patient identifier PID.R.

The next step of these embodiments is the optional step of verifying VER-REQ the request REQ for the requested medical data record MDR.R with the computation unit PSYS.CU of the providing system PSYS. In particular, within the step of verifying VER-REQ the request REQ is checked whether the database DB.1, . . . , DB.3 actually comprises the requested medical data record MDR.R. In particular, the requested medical data record MDR.R is one of the medical data records MDR.1, . . . , MDR.3 stored in the database DB.1, . . . , DB.3 corresponding to the request patient identifier PID.R.

If the request REQ comprises the request patient identifier PID.R, verifying VER-REQ the request REQ can comprise querying the database DB.1, . . . , DB.3 to check whether the database DB.1, . . . , DB.3 stores a medical data record MDR.1, . . . , MDR.3 related to the request patient identifier PID.R, which is then by definition the requested medical data record MDR.R. If the request REQ comprises the the salted hash H(PID.R & SLT) of the request patient identifier PID.R, verifying VER-REQ the request REQ can comprise calculating the salted hashes H(PID.1, SLT), . . . , H(PID.3, SLT) of the patient identifiers PID.1, . . . , PID.3 stored in the database DB.1, . . . , DB.3, and comparing the salted hash H(PID.R & SLT) of the request patient identifier PID.R with the salted hashes H(PID.1, SLT), . . . , H(PID.3, SLT) of the patient identifiers PID.1, . . . , PID.3 for equivalence. In this case, the check is positive if an identical salted hash H(PID.1, SLT), . . . , H(PID.3, SLT) of the patient identifiers PID.1, . . . , PID.3 is found.

If the request REQ comprises a signature SGN(SLT, PRK.R) signed with a private key PRK.R related to the request patient identifier PID.R, verifying VER-REQ the request REQ can comprise verifying the signature SGN (SLT, PRK.R) based on the public key related to the private key PRK.R. In this embodiment, the public key related to the private key PRK.R is related, in particular identical with or directly derivable from the request patient identifier PID.R.

If the step of verifying VRF-REQ the request REQ results in a negative result, the method ends. If the step of verifying VRF-REQ the request REQ results in a positive result, the last step of the displayed embodiment is providing PROV-MDR.R the requested medical data record MDR.R to the receiving entity RE via a secure communication channel with the interface PSYS.IF of the providing system PSYS. The step of providing PROV-MDR.R the requested medical data record MDR.R can comprise querying the database DB.1, . . . , DB.3 for the requested medical data record MDR.R.

Figure 13:
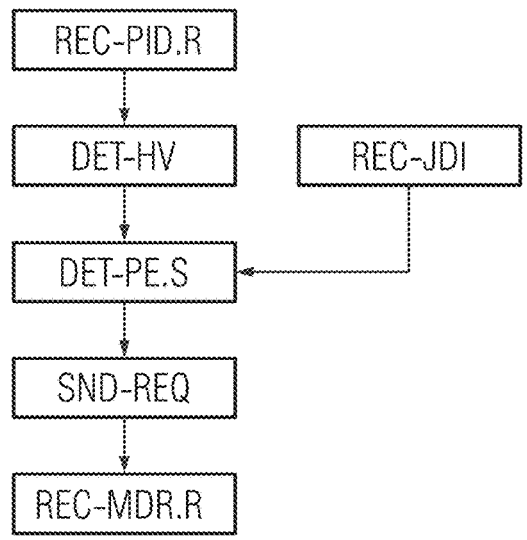

FIG. 13 displays a flow chart of an embodiment of the method for receiving a requested medical data record MDR.R related to a patient PAT from a selected providing entity PE.S.

The first step of the displayed method is receiving REC-PID.R a request patient identifier PID.R corresponding to the patient PAT with an interface RSYS.IF of the receiving system RSYS. In this embodiment, the request patient identifier PID.R is stored in a device DEV (e.g. a smartphone) of the patient PAT, and the patient identifier PID.R is received from the device DEV by the interface RSYS.IF. For example, the request patient identifier PID.R can be transmitted via Bluetooth, via WiFi or by displaying a barcode or an QR-Code on the device DEV of the patient, which is optically transmitted to the interface RSYS.IF of the receiving system.

The next step of the displayed method is receiving REC-JDI a set of joint data indices JDI.1, . . . , JDI.3 with the interface RSYS.IF of the receiving system RSYS, wherein each joint data index JDI.1, . . . , JDI.3 of the joint data indices JDI.1, . . . , JDI.3 corresponds to a providing entity PE.1, . . . , PE.3 from a group of providing entities PE.1, . . . , PE.3.

For each of the providing entities PE.1, . . . , PE.3 the corresponding joint data index JDI.1, . . . , JDI.3 is a Bloom filter indicative of patient identifiers PID.1, . . . , PID.3 stored by the providing entity PE.1, . . . , PE.3 related to the medical data records MDR.1, . . . , MDR.3. This means that based on the joint data index JDI.1, . . . , JDI.3 it can be determined that the corresponding providing entity PE.1, . . . , PE.3 does not store a medical data record MDR.1, . . . , MDR.3 related to the request patient identifier PID.R, but it cannot be determined for sure that the corresponding providing entity PE.1, . . . , PE.3 does store a medical data record MDR.1, . . . , MDR.3 related to the request patient identifier PID.R.

In this embodiment, the joint data indices JDI.1, . . . , JDI.3 are stored within a distributed ledger LDG, and receiving REC-JDI a set of joint data indices JDI.1, . . . , JDI.3 is executed by querying the distributed ledger LDG. Alternatively, the joint data indices JDI.1, . . . , JDI.3 can also be stored only with the respective providing entities PE.1, . . . , PE.3, and receiving REC-JDI joint data indices JDI.1, . . . , JDI.3 can comprise querying each of the respective providing entities PE.1, . . . , PE.3 for the joint data indices JDI.1, . . . , JDI.3.

The next step of the displayed embodiment is determining DET-HV a hash vector HV.4, HV.5 by applying a group of hash functions h1, h2 to the request patient identifier PID.R. Details of determining the hash vector HV.4, HV.5 were described with respect to FIG. 1 to FIG. 4. In particular, the hash vector HV.4, HV.5 and each joint data index JDI.1, . . . , JDI.3 of the joint data indices JDI.1, . . . , JDI.3 comprise the same number of data elements, and each joint data index JDI.1, . . . , JDI.3 of the joint data indices JDI.1, . . . , JDI.3 has been created by the respective providing entity PE.1, . . . , PE.3 by the group of hash functions h1, h2 used in determining DET-HV the hash vector HV.4, HV.5.

Alternatively, each of the providing entities PE.1, . . . , PE.3 may use different hash functions h1, h2 to determine the respective joint data index JDI.1, . . . , JDI.3. In this case, in the step of determining DET-HV the hash vector HV.4, HV.5 for each of the joint data index JDI.1, . . . , JDI.3 a different set of hash functions h1, h2 has to be used. In this case, it is also possible that the joint data indices JDI.1, . . . , JDI.3 comprise different numbers of elements.

The next step of the displayed embodiment is determining DET-PE.S a selected providing entity PE.S of the group of providing entities PE.1, . . . , PE.3 based on the hash vector HV.4, HV.5 and based on the joint data indices JDI.1, . . . , JDI.3. In particular, the selected providing entity PE.S is one of the providing entities PE.1, . . . , PE.3 of the group of providing entities PE.1, . . . , PE.3. Within this step, it is also possible that several selected providing entities PE.S are determined. In particular, the selected providing entity PE.S is one of the several selected providing entities PE.S determined within this determining DET-PES.S step.

Within this embodiment, the step of determining DET-PE.S the selected providing entity PE.S comprises an elementwise comparison between the hash vector HV.4, HV.5 and each of the joint data indices JDI.1, . . . , JDI.3. This elementwise comparison is described with respect to FIG. 3 and FIG. 4.

The next step of the displayed embodiment is sending SND-REQ a request REQ for the requested medical data record MDR.R to the selected providing entity PE.S. In this embodiment, the request REQ comprises a salted hash H(PID.R & SLT) of the request patient identifier PID.R and a signature SGN(SLT, PRK.R) signed with a private key PRK.R related to the request patient identifier PID.R. Alternatively, the request REQ can comprise a salted hash H(PID.R & SLT) of the request patient identifier PID.R, but no signature SGN(SLT, PRK.R) signed with the private key PRK.R related to the request patient identifier PID.R. Alternatively, the request REQ can comprise a signature SGN (SLT, PRK.R) signed with the private key PRK.R related to the request patient identifier PID.R, but no salted hash of the request patient identifier PID.R. Alternatively, the request REQ can neither comprise a salted hash H(PID.R & SLT) of the request patient identifier PID.R nor a signature SGN (SLT, PRK.R) signed with a private key PRK.R related to the request patient identifier PID.R. A method for creating and exchanging the salted hash H(PID.R & SLT) of the request patient identifier PID.R is explained with respect to FIG. 8, a method for creating an exchanging the signature SGN(SLT, PRK.R) signed with the private key PRK.R related to the request patient identifier PID.R is explained with respect to FIG. 9. Alternatively to the salted hash H(PID.R & SLT) of the request patient identifier PID.R, the request REQ can also comprise the request patient identifier PID.R.

The last step of the displayed embodiment is receiving REC-MDR.R the requested medical data record MDR.R from the selected providing entity PE.S via a secure communication channel. Note that this step is only executed if the selected providing entity PE.S in fact stores the requested medical data record MDR.R corresponding to the request patient identifier PID.R. If the selected providing entity PE.S does not store the requested medical data record MDR.R, the providing entity PE.S can send an error message or not send any data at all.

Figure 14:
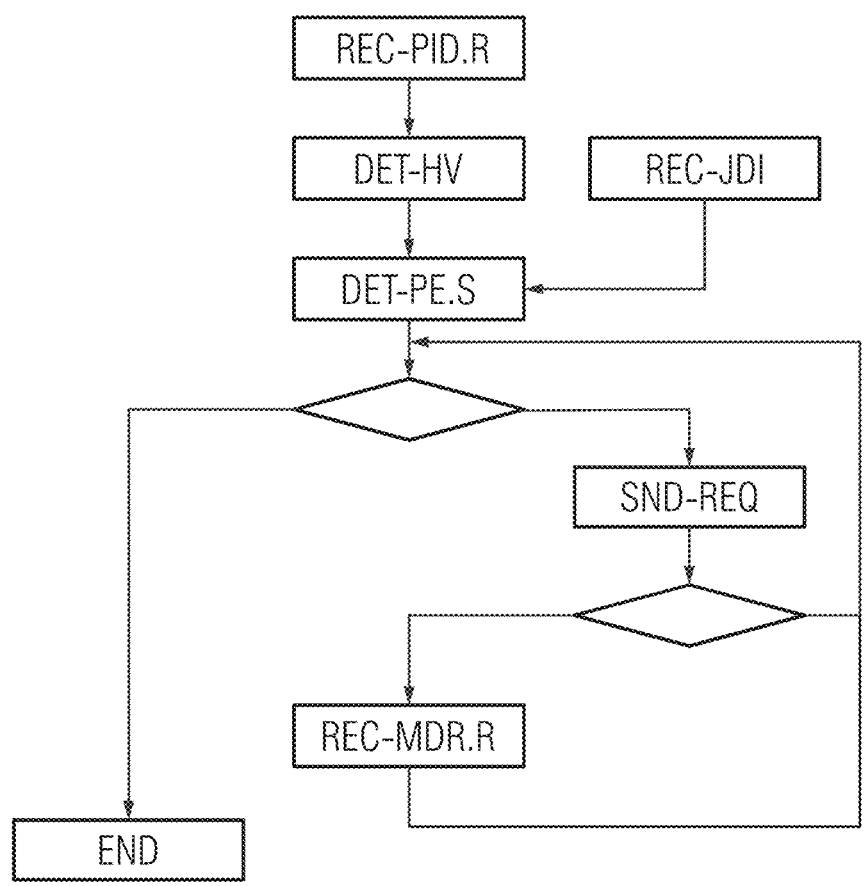

FIG. 14 displays a flow chart of a modified embodiment of the method for receiving a requested medical data record MDR.R related to a patient PAT from a selected providing entity PE.S. The single steps of the flow chart are analogue to the embodiment described related to FIG. 13, but additional control structures are indicated in FIG. 14 to display a possibility for applying the method for receiving a requested medical data record MDR.R in the case a plurality of selected providing entities PE.S is determined in the step of determining DET-PE.S a selected providing entity PE.S.

In the displayed embodiment, for each of the determined selected providing entities PE.S the step of sending SND-REQ a request REQ for the requested medical data record MDR.R to the corresponding selected providing entity PE.S is executed. After sending SND-REQ a request REQ for the requested medical data record MDR.R to the corresponding selected providing entity PE.S, in case the corresponding selected providing entity PE.S provides a requested medical data record MDR.R, the step of receiving REC-MDR.R the requested medical data record MDR.R from the corresponding selected providing entity PE.S is executed, otherwise the flowchart continues with the next selected providing entity PE.S. After a request REQ has been sent to all of the selected providing entities PE.S, the method ends END.

Figure 15:
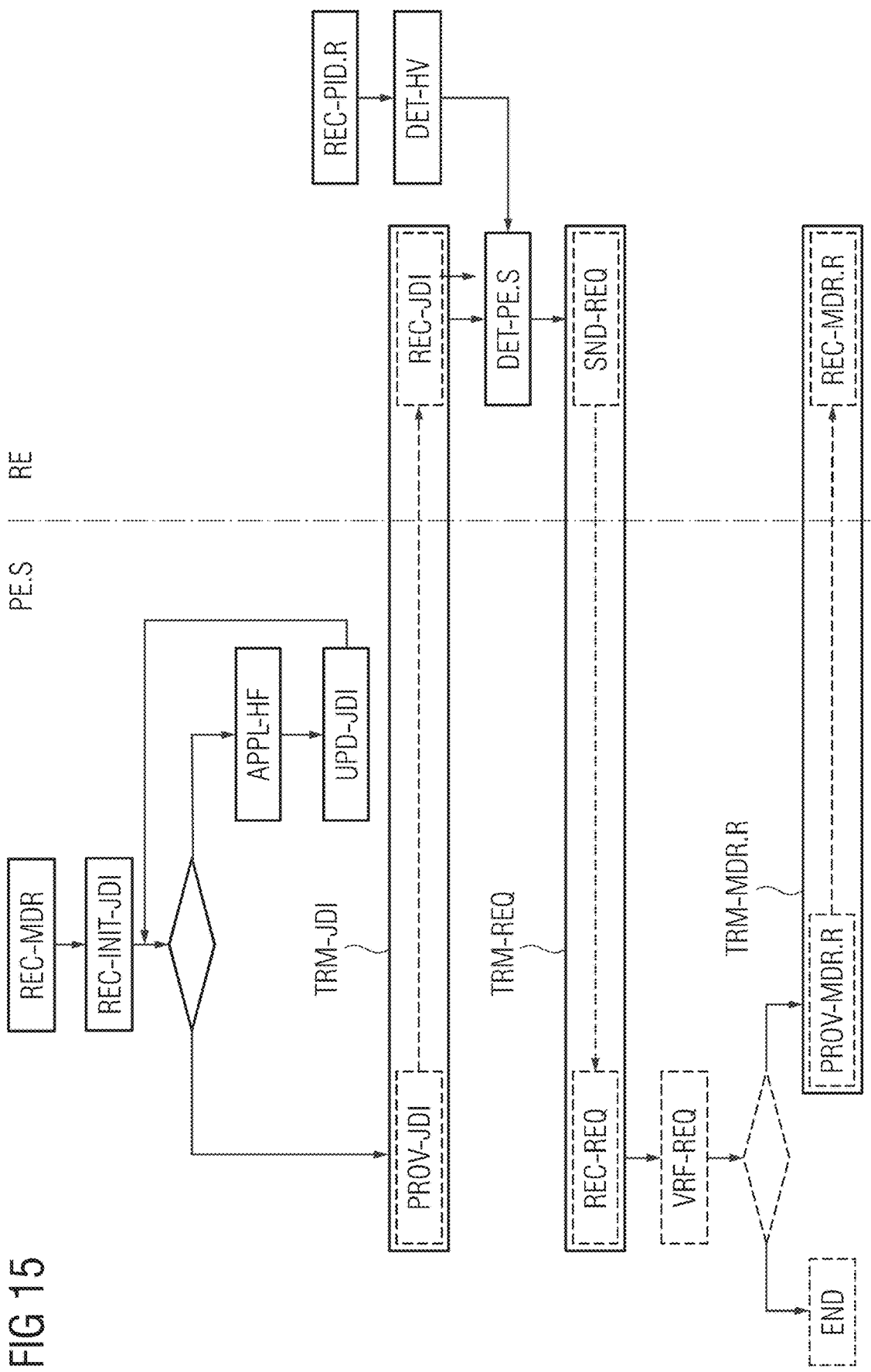

FIG. 15 displays an embodiment of the method for transmitting a requested medical data record MDR.R from a selected providing entity PE.S to a receiving entity RE. This embodiment be interpreted as a combination of the embodiments described with respect to FIG. 11 and Y2. In particular, each of the steps executed in the embodiment of the method for transmitting a requested medical data record MDR.R from a selected providing entity PE.S to a receiving entity RE can comprise all advantageous features and embodiments described with respect to the respective steps of the embodiments described with respect to FIG. 11 and Y2.

In particular, the embodiment comprises the step of transmitting TRM-JDI the joint data index JDI.0, . . . , JDI.4 from the selected providing entity PE.S to the receiving entity RE, in particular with the interface PSYS.IF of the providing system PSYS and the interface RSYS.IF of the receiving system RSYS. The step of transmitting TRM-JDI the joint data index JDI.0, . . . , JDI.4 from the selected providing entity PE.S to the receiving entity RE can comprise the steps of providing PROV-JDI the joint data index JDI.0, . . . , JDI.4 to the receiving entity RE and receiving the joint data index JDI.0, . . . , JDI.4 from the selected providing entity PE.S.

In particular, the embodiment comprises the step of transmitting TRM-REQ a request REQ for the requested medical data record MDR.R from the receiving entity RE to the selected providing entity PE.S with the interface PSYS.IF of the providing system PSYS and the interface RSYS.IF of the receiving system RSYS. The step of transmitting TRM-REQ the request REQ for the requested medical data record MDR.R from the receiving entity RE to the selected providing entity PE.S can comprise the steps of providing PROV-REQ the request REQ for the requested medical data record MDR.R to the selected providing entity PE.S and of receiving REC-REQ the request REQ for the requested medical data record MDR.R from the receiving entity RE.

In particular, the embodiment comprises the step of transmitting TRM-MDR.R the requested medical data record MDR.R from the selected providing entity PE.S to the receiving entity RE via a secure communication channel with the interface PSYS.IF of the providing system PSYS and the interface RSYS.IF of the receiving system RSYS. In particular, the step of transmitting TRM-MDR.R the requested medical data record MDR.R from the selected providing entity PE.S to the receiving entity RE via the secure communication channel can comprise the steps of providing PROV-MDR.R the requested medical data record MDR.R to the receiving entity RE and of receiving REC-MDR.R the requested medical data record MDR.R from the selected providing entity PE.S.

Figure 16:
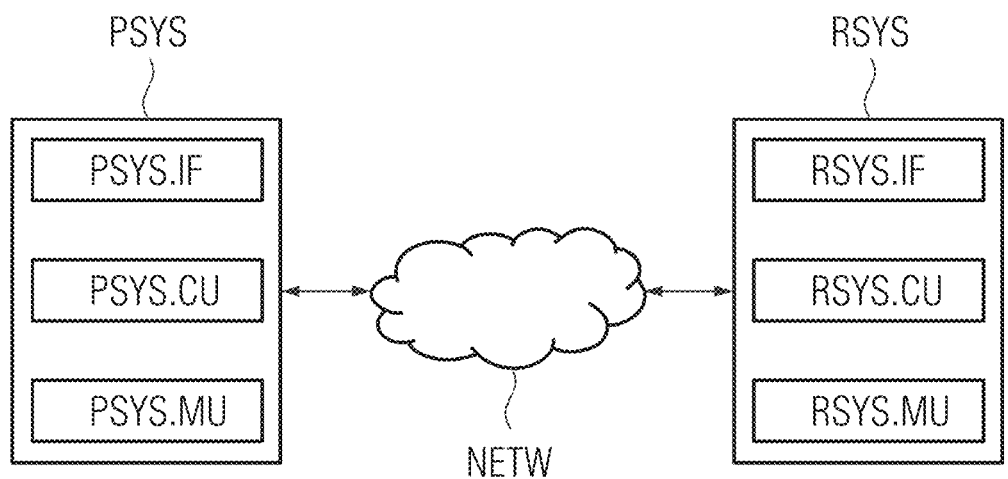

FIG. 16 displays a providing system PSYS and a receiving system RSYS. The providing system PSYS comprises an interface PSYS.IF, a computation unit PSYS.CU, and a memory unit PSYS.MU. The receiving system RSYS comprises an interface RSYS.IF, a computation unit RSYS.CU, and a memory unit RSYS.MU.

The providing system PSYS and/or the receiving system RSYS can be a (personal) computer, a workstation, a virtual machine running on host hardware, a microcontroller, or an integrated circuit. In particular, the providing system PSYS and/or the receiving system RSYS can be mobile devices, e.g. a smartphone or a tablet. As an alternative, the providing system PSYS and/or the receiving system RSYS can be a real or a virtual group of computers (the technical term for a real group of computers is "cluster", the technical term for a virtual group of computers is "cloud").

The providing system PSYS and the receiving system RSYS are connected by a network NETW. The network NETW can be realized as a LAN (acronym for "local area network"), in particular a WiFi network, or any other local connection, e.g. via Bluetooth or USB (acronym for "universal serial bus"). The network NETW can alternatively also be realized as a VPN (acronym for "virtual private network").

An interface PSYS.IF, RSYS.IF can be embodied as a hardware interface or as a software interface (e.g. PCIBus, USB or Firewire). In particular, the interface PSYS.IF, RSYS.IF can be a combination of several other interfaces, in particular, the interface PSYS.IF, RSYS.IF can comprise one or more interfaces as subcomponent. In general, a computation unit PSYS.CU, RSYS.CU can comprise hardware elements and software elements, for example a microprocessor, a CPU (acronym for "central processing unit"), a GPU (acronym for "graphical processing unit"), a field programmable gate array (an acronym is "FPGA") or an ASIC.(acronym for "applicationspecific integrated circuit"). The calculation unit PSYS.CU, RSYS.CU can be configured for multithreading, i.e. the calculation unit PSYS.CU, RSY-S.CU can host different calculation processes at the same time, executing the either in parallel or switching between active and passive calculation processes. In particular, the computation unit PSYS.CU, RSYS.CU can be a combination of several other computation units, in particular, the computation unit PSYS.CU, RSYS.CU can comprise one or more computation units as subcomponents. A memory unit PSYS.MU, RSYS.MU can be e.g. non-permanent main memory (e.g. random access memory) or permanent mass storage (e.g. hard disk, USB stick, SD card, solid state disk).

Wherever not already described explicitly, individual embodiments, or their individual embodiments and features, can be combined or exchanged with one another without limiting or widening the scope of the described invention, whenever such a combination or exchange is meaningful and in the sense of this invention. Advantages which are described with respect to one embodiment of the present invention are, wherever applicable, also advantageous of other embodiments of the present invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for providing a requested medical data record to a receiving entity, comprising:
   receiving a set of medical data records stored in a database of a providing entity;
   receiving or initializing a joint data index;
   for each respective medical data record of the set of medical data records
      applying a plurality of hash functions to a patient identifier corresponding to the respective medical data record to determine a respective hash vector, the patient identifier corresponding to the respective medical data record identifying a patient being subject of the respective medical data record, and
      updating the joint data index based on the respective hash vector;
   providing the joint data index to the receiving entity, wherein the providing the joint data index includes storing, by the providing entity, the joint data index in a distributed ledger that is accessible by the receiving entity;
   receiving a request for the requested medical data record of the set of medical data records from the receiving entity, the request being based on the provided joint data index and the requested medical data record corresponding to a requested patient identifier; and
   providing the requested medical data record to the receiving entity via a secure communication channel.

2. The computer-implemented method of claim 1, wherein each of the respective hash functions maps the patient identifier to one element of the hash vector.

3. The computer-implemented method of claim 2, wherein the joint data index provided to the receiving entity is a Bloom filter of the patient identifiers corresponding to the set of medical data records stored in the database.

4. The computer-implemented method of claim 3, wherein the Bloom filter is at least one of a counting Bloom filter, a scalable Bloom filter, a layered Bloom filter and an attenuated Bloom filter.

5. The computer-implemented method of claim 1, wherein the joint data index provided to the receiving entity is a Bloom filter of the patient identifiers corresponding to the set of medical data records stored in the database.

6. The computer-implemented method of claim 5, wherein the Bloom filter is at least one of a counting Bloom filter, a scalable Bloom filter, a layered Bloom filter and an attenuated Bloom filter.

7. The computer-implemented method of claim 1, wherein the request comprises at least one of a salted hash of the request patient identifier and a signature signed with a private key related to the request patient identifier.

8. A non-transitory computer program product storing instructions of a program which, when the program is executed by a providing system, cause the providing system to carry out the method of claim 1.

9. A non-transitory computer-readable medium storing instructions of a program which, when executed by a providing system, cause the providing system to carry out the method of claim 1.

10. The computer-implemented method of claim 1, further comprising, prior to the providing:
    verifying the request for the requested medical data record.

11. A computer-implemented method for sending a request for a requested medical data record of a patient, comprising:
    receiving a request patient identifier corresponding to the patient;
    receiving a set of joint data indices by querying a distributed ledger storing the set of joint data indices, each respective joint data index of the set of joint data indices respectively corresponding to a respective providing entity from a group of providing entities, wherein each respective joint data index of the set of joint data indices is based on a plurality of hash functions and each respective joint data index is stored in the distributed ledger by the respective providing entity, the distributed ledger being accessible by a receiving entity;
    determining a hash vector by applying the plurality of hash functions to the request patient identifier;
    determining a selected providing entity of the group of providing entities based on the hash vector and based on the joint data indices; and
    sending a request for the requested medical data record to the selected providing entity.

12. The computer-implemented method of claim 11, wherein the determining of the selected providing entity comprises an elementwise comparison between the hash vector and each of the set of joint data indices.

13. The computer-implemented method of claim 11, wherein each respective joint data index of the set of joint data indices is a Bloom filter of patient identifiers corresponding to medical data records stored by the providing entity corresponding to the respective joint data index.

14. The computer-implemented method of the claim 11, wherein the requested medical data record is provided by the selected providing entity according to a computer-implemented method, comprising:
   receiving a set of medical data records stored in a database;
   receiving or initializing a joint data index;
   for each respective medical data record of the set of medical data records
      applying a plurality of hash functions to a patient identifier corresponding to the respective medical data record to determine a respective hash vector, the patient identifier corresponding to the respective medical data record identifying the patient being subject of the respective medical data record, and
      updating the joint data index based on the respective hash vector;
   providing the joint data index to a receiving entity;
   receiving a request for the requested medical data record from the receiving entity, the request being based on the joint data index and the requested medical data record corresponding to a request patient identifier; and
   providing the requested medical data record to the receiving entity via a secure communication channel.

15. The computer-implemented method of claim 11, further comprising, after the sending:
   receiving the requested medical data record from the selected providing entity via a secure communication channel.

16. A non-transitory computer-readable medium storing instructions of a program which, when executed by a receiving system, cause the receiving system to carry out the method of claim 11.

17. A providing system for providing a requested medical data record to a receiving entity, comprising:
   an interface, configured to receive a set of medical data records stored in a database of a providing entity; and
   a computation unit, wherein the interface or the computation unit is configured to receive or initialize a joint data index and wherein the computation unit is, for each respective medical data record of the set of medical data records,
      configured to apply a plurality of hash functions to a patient identifier corresponding to the respective medical data record to determine a respective hash vector, the patient identifier corresponding to the respective medical data record identifying a patient being subject of the respective medical data record, and
      configured to update the joint data index based on the respective hash vector;
   wherein the interface is furthermore configured to provide the joint data index to the receiving entity by storing, by the providing entity, the joint data index in a distributed ledger that is accessible by the receiving entity,
   wherein the interface is furthermore configured to receive a request for the requested medical data record of the set of medical data records from the receiving entity,
   wherein the requested medical data record corresponds to a requested patient identifier, and
   wherein the interface is furthermore configured to provide the requested medical data record to the receiving entity via a secure communication channel.

18. The providing system of claim 17, wherein the computation unit is configured to verify the request for the requested medical data record prior to the interface providing the requested medical data record to the receiving entity via the secure communication channel.

* * * * *